(12) United States Patent
Geist et al.

(10) Patent No.: US 8,333,771 B2
(45) Date of Patent: Dec. 18, 2012

(54) SYSTEM FOR PUSHING AND PULLING SURGICAL IMPLANTS INTO POSITION IN VIVO VIA A TETHER

(75) Inventors: Wyatt Drake Geist, Davie, FL (US); Christopher Walsh, Parkland, FL (US)

(73) Assignee: Magrod, LLC, Davie, FL (US)

( * ) Notice: Subject to any disclaimer, the term of this patent is extended or adjusted under 35 U.S.C. 154(b) by 0 days.

(21) Appl. No.: 13/313,765

(22) Filed: Dec. 7, 2011

(65) Prior Publication Data

US 2012/0179214 A1   Jul. 12, 2012

Related U.S. Application Data

(63) Continuation-in-part of application No. 13/313,528, filed on Dec. 7, 2011, which is a continuation of application No. 12/728,818, filed on Mar. 22, 2010, now Pat. No. 8,092,461, which is a continuation-in-part of application No. 12/157,397, filed on Jun. 10, 2008, now Pat. No. 7,976,546, which is a continuation-in-part of application No. 13/151,756, filed on Jun. 2, 2011, which is a continuation-in-part of application No. 11/462,592, filed on Aug. 4, 2006, now Pat. No. 8,092,458, which is a continuation of application No. 12/338,794, filed on Dec. 18, 2008, now Pat. No. 8,092,460.

(51) Int. Cl.
*A61B 17/58* (2006.01)
*A61B 17/60* (2006.01)
*A61B 17/70* (2006.01)
*A61F 2/00* (2006.01)

(52) U.S. Cl. ........................................ 606/86 A; 606/99

(58) Field of Classification Search ................. 606/86 A, 606/86 B, 86 R, 99, 914–916, 246
See application file for complete search history.

(56) References Cited

U.S. PATENT DOCUMENTS

| | | |
|---|---|---|
| 5,049,151 A | 9/1991 | Durham et al. |
| 5,127,913 A | 7/1992 | Thomas, Jr. |
| 5,514,145 A | 5/1996 | Durham et al. |
| 5,797,911 A | 8/1998 | Sherman et al. |
| 5,851,183 A | 12/1998 | Bucholz |
| 6,074,394 A | 6/2000 | Krause |
| 6,086,596 A | 7/2000 | Durham |
| 6,127,597 A | 10/2000 | Beyar et al. |
| 6,162,228 A | 12/2000 | Durham |
| 6,168,595 B1 | 1/2001 | Durham et al. |
| 6,226,548 B1 | 5/2001 | Foley et al. |
| 6,236,875 B1 | 5/2001 | Bucholz et al. |
| 6,503,249 B1 | 1/2003 | Krause |

(Continued)

FOREIGN PATENT DOCUMENTS

WO    WO 2009105104    8/2009

(Continued)

*Primary Examiner* — Sameh Boles
(74) *Attorney, Agent, or Firm* — McHale & Slavin, P.A.

(57) ABSTRACT

The present invention describes a system suitable for guiding a biocompatible device to a target area within the body (in vivo) and method of using the same. The system includes a targeting member being constructed of, or having a steering material, which can be coupled to a biocompatible device. The system further includes one or more devices which are used to maneuver the targeting member into position prior to attachment of the biocompatible device. The biocompatible device is traversed into position through the passageway created by the targeting member and secured to one or more anchoring members.

17 Claims, 23 Drawing Sheets

U.S. PATENT DOCUMENTS

| | | |
|---|---|---|
| 7,011,660 B2 | 3/2006 | Sherman et al. |
| 7,835,778 B2 | 11/2010 | Foley et al. |
| 7,976,546 B2 | 7/2011 | Geist et al. |
| 8,092,458 B2 | 1/2012 | Geist et al. |
| 8,092,460 B2 | 1/2012 | Geist et al. |
| 8,092,461 B2 | 1/2012 | Geist et al. |
| 2003/0065373 A1 | 4/2003 | Lovett et al. |
| 2005/0055089 A1 | 3/2005 | Macoviak et al. |
| 2005/0075562 A1 | 4/2005 | Szakelyhidi, Jr. et al. |
| 2005/0085714 A1 | 4/2005 | Foley et al. |
| 2005/0277934 A1 | 12/2005 | Vardiman |
| 2006/0079894 A1 | 4/2006 | Colleran et al. |
| 2006/0149135 A1 | 7/2006 | Paz |
| 2007/0191836 A1 | 8/2007 | Justis |
| 2007/0191845 A1 | 8/2007 | Justis et al. |
| 2007/0213714 A1 | 9/2007 | Justis |
| 2008/0039845 A1 | 2/2008 | Bonutti et al. |
| 2008/0140100 A1 | 6/2008 | Gertner |
| 2008/0312704 A1 * | 12/2008 | Hestad et al. ............... 606/86 A |
| 2009/0287255 A1 | 11/2009 | Erickson et al. |
| 2011/0238117 A1 | 9/2011 | Geist et al. |

FOREIGN PATENT DOCUMENTS

| | | |
|---|---|---|
| WO | WO 2009152243 | 12/2009 |

* cited by examiner

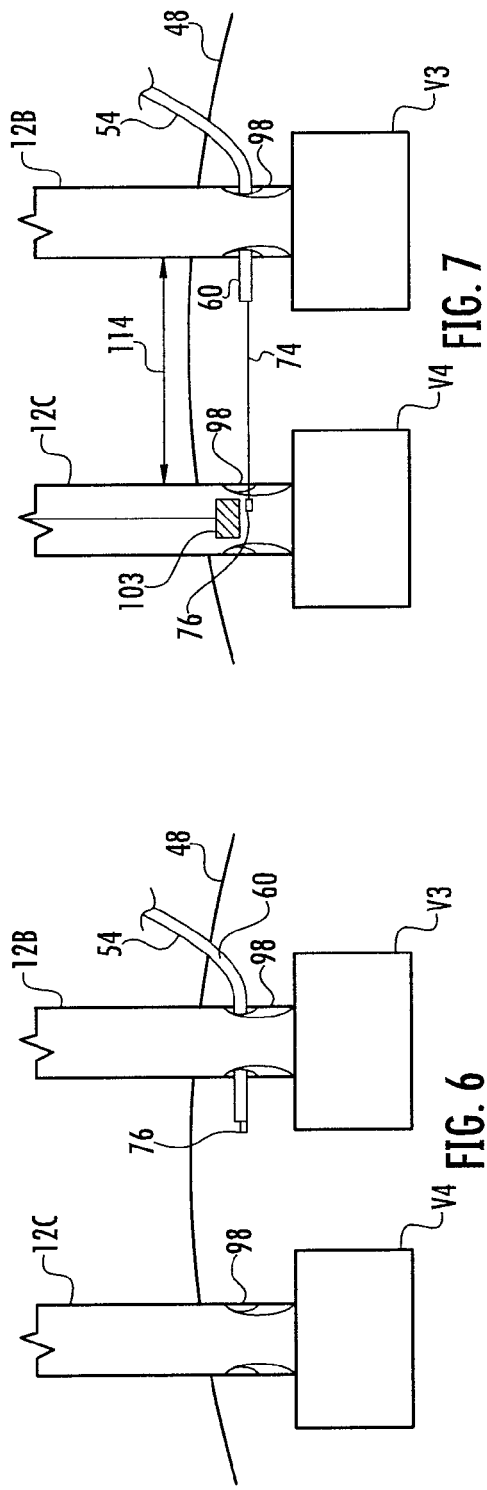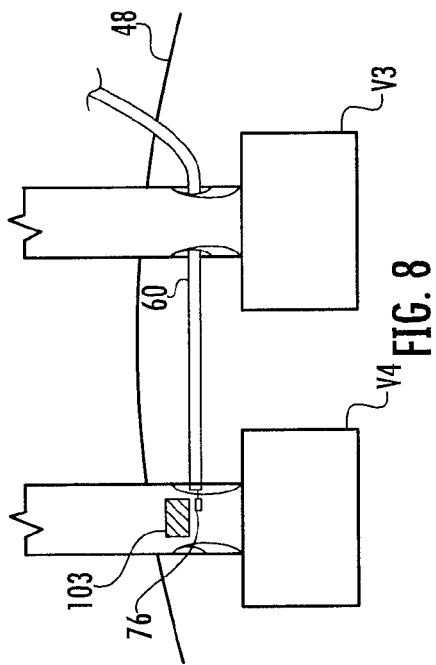

SYSTEM FOR PUSHING AND PULLING SURGICAL IMPLANTS INTO POSITION IN VIVO VIA A TETHER

CROSS REFERENCE TO RELATED APPLICATIONS

This application is a continuation-in-part of U.S. application Ser. No. 13/313,528, filed Dec. 7, 2011, entitled "Method and Apparatus for Facilitating Navigation of an Implant", which is a continuation of U.S. application Ser. No. 12/728,818, filed on Mar. 22, 2010, entitled "Method and Apparatus For Facilitating Navigation of An Implant", which is now U.S. Pat. No. 8,092,461, which is a continuation-in-part of U.S. application Ser. No. 12/157,397, filed on Jun. 10, 2008, entitled "Magnetic Targeting System for Facilitating Navigation", which is now issued U.S. Pat. No. 7,976,546, on Jun. 22, 2011, which is a continuation-in-part of U.S. application Ser. No. 13/151,756, filed on Jun. 2, 2011, entitled "Magnetic Targeting System For Facilitating Navigation", which is a continuation-in-part of U.S. application Ser. No. 11/462,592 filed on Aug. 4, 2006, entitled "Magnetic Targeting System and Method of Using The Same", which is now U.S. Pat. No. 8,092,458, which is a continuation of U.S. application Ser. No. 12/338,794, filed on Dec. 18, 2008, entitled "Magnetic Targeting System and Method of Using the Same", which is now U.S. Pat. No. 8,092,460, each of which are hereby expressly incorporated by reference.

FIELD OF THE INVENTION

The invention generally relates to surgical implants; particularly to a system and method for stabilization of adjacent bony structures; most particularly to a system to help navigate an interconnecting means between multiple bony stabilization devices.

BACKGROUND OF THE INVENTION

It is widely held that healing and/or structural correction is greatly facilitated when a bone is stabilized in the proper position. Various devices for stabilization of bone are well known and routinely practiced in the medical arts. For example, an abnormal spine can be stabilized using a substantially rigid or semi-rigid interconnecting means (rod or plate) and fastening means (screws, clamps, hooks, claws, anchors, or bolts). Multiple fasteners are placed into the spinal pedicle of each vertebra and linked by at least one interconnecting means. One of the more difficult aspects is the surgical insertion of the interconnecting means along a fixed path of delivery longitudinally along the vertebrae and through each of the multiple fastening means between multiple vertebrae. Once in place, this system substantially immobilizes the spine and promotes bony fusion (arthrodesis).

Traditionally, the surgical techniques for stabilization of bone required large incisions (upwards of 6 cm in length) and a considerable amount of muscle be cut and stripped away (retracted) from the bone for an "open" visualization of the bone and access thereto for the placement of the fasteners and instrument implantation. Although this so-called "open" surgical technique has successfully treated non-unions, instability, injuries and disease of the spine, it is not without disadvantages. Given the invasive nature of this technique, a lengthy healing time and considerable post-operative pain for the patient is common.

In response to aforementioned drawbacks, the surgical arts have developed minimally invasive systems and procedures intended to replace the more traditional open surgeries. Obviously, a less extensive system and procedure will eliminate the need to perform much of the cutting and stripping of muscle, resulting in reduced recovery time and less post-operative pain. As a result, percutaneous procedures have been developed which insert instruments and perform operations through small skin incisions, usually between 1.5 and 5 cm in length, thereby reducing soft tissue damage. However, smaller skin incisions and smaller surgical fields require more novel and innovative approaches to perform these complicated surgeries.

One such example of a minimally invasive system is the SEXTANT Spinal System by Medtronic (Memphis, Tenn.). This device is comprised of two basic components, screw extenders and the rod inserter, which results in an instrument that looks like a sextant used in naval navigation. The device is an insertion tool that allows fasteners and interconnecting means to be applied to the spine in a minimally invasive manner. The screw extenders are long shafts used to deliver and attach screws to the vertebrae through small skin incisions. During surgery, these extenders protrude outside the body, allowing the surgeon to arrange and join their ends so that the rod inserter may be attached. The rod inserter is an arc-shaped arm that swings along a fixed axis and pushes an interconnecting rod though the skin and muscle and into the heads of the implanted fasteners (pedicle screws).

While the aforementioned technique is adequate when the fastening means are well aligned, it fails to deliver the rod when one of the screws is misaligned. Moreover, the interconnecting rod must be pushed by the surgeon along a fixed arch and cannot be directed around neural structures or bony obstructions. One consequence of forcibly pushing the rod through the fastening means is the possibility of collision between the rod and a bony obstruction causing a piece of bone to break off, resulting in possible neurological damage. Another common problem is the interconnecting rod becoming disengaged from the rod inserter. When either of these incidents happens, additional surgery is often required to remove the bone fragment and rod from the wound. This may result in the surgeon abandoning the minimally invasive approach and reverting to a traditional approach. Current spinal implant systems do not allow the contour of the rod to match the normal curvature of the surrounding anatomy, and such systems are not customizable to meet the individual anatomical variables that each patient presents.

In order to help avoid damaging sensitive anatomy and expedite implant assembly, various image-based navigation systems have been employed which utilize patient images obtained prior to or during the medical procedure to guide a surgeon during the surgery. Recent advances in imaging technology have produced detailed two and three dimensional images using optically guided, fluoroscopic guided, and electromagnetic field based systems. These image-based systems have also been used in combination with the previously described "open" surgeries. One significant problem with most image-based systems is that the radiation generated is transmitted to the patient and surgical staff, which may result in physiological damage over time. Also, the cost and portability of this equipment continue to be an issue. In addition, these systems often require the surgeon undergo extensive training to operate correctly.

Accordingly, a need exists in the surgical arts for a system and minimally invasive procedure capable of providing optimal mechanical support and bony fusion, while reducing the likelihood of bone damage and neural functioning when compared to the currently available interconnecting elements. It is also desirable to provide a surgical procedure that can be performed in conjunction with, but does not require, an image-based tracking system.

PRIOR ART

Although there are numerous patents directed to systems and methods for insertion of a stabilizing implant at a selected area of an anatomy, the prior art nevertheless fails to teach a targeting system for the insertion of an implant using minimally invasive techniques having a decreased risk of causing damage to neural structures or bony obstructions using minimal, if any, radiation exposure to the patient and/or surgeon.

For example, U.S. Publication No. 2005/0085714 to Foley et al., discloses a method and apparatus for percutaneous and/or minimally invasive implantation of a construct (e.g., spinal implant). The construct may be implanted using a navigation system for planning and execution of a procedure. A plurality of portions of the construct may be interconnected using locations and paths determined and navigated with the navigation system. The navigation system utilizes optical or electromagnetic localization to determine the precise location of a selected implant construct or instrument. An optical localizer can be positioned relative to an extender attached to a screw. Alternatively, a coil may be positioned in an electromagnetic (EM) field such that the position of the coil may be determined by sensing the induced voltage. A computer is used to form a plan prior to implantation of the construct and thereafter track the various portions of the construct during insertion. The plan and the tracking of the surgery are displayed on a monitor to provide guidance to the surgeon.

U.S. Publication No. 2005/0277934 to Vardiman, discloses a minimally invasive spinal fixation system used for spinal arthrodesis (bony fusion) or motion preservation. The system comprises a plurality of pedicle screws, including a first screw placed into a first vertebral body, and a second screw placed into a second vertebral body, a connector for attaching to the first and second screws and, a removable guide for percutaneously attaching the connector to the first and second screws. According to one embodiment, detectional spheres are positioned on the head of screw extenders and on the handle of the rod insertion tool. A comparator calculates the relative position of the insertion tool handle with respect to the screw extenders and provides a visual display for the surgeon.

U.S. Pat. No. 6,236,875 to Bucholz, discloses surgical navigation systems including reference and localization frames. The system generates an image representing the position of one or more body elements during the procedure using magnetic resonance imaging (hereinafter, MRI) or computed tomography (hereinafter, CT) scan images taken prior to the surgery. The body elements and their relative position are identified during the procedure. The position of the known body elements can then be manipulated using a computer to the relative position of the patient during the surgery. The manipulated data can then be utilized to guide the surgeon for implantation.

U.S. Pat. No. 6,226,548 to Foley et al., discloses an apparatus and procedures for percutaneous placement of surgical implants and instruments such as, for example, screws, rods, wires and plates into various body parts using image guided surgery. The invention includes an apparatus for use with a surgical navigation system, an attaching device rigidly connected to a body part, such as the spinous process of a vertebra, with an identification superstructure rigidly but removable connected to the attaching device. This identification superstructure, for example, is a reference arc and fiducial array which accomplishes the function of identifying the location of the superstructure, and, therefore, the body part to which it is fixed, during imaging by CT scan or MRI, and later during medical procedures. The system utilizes emitters such as light emitting diodes (hereinafter, LEDs), passive reflective spheres, acoustics, magnetics, electromagnetics, radiologic, or micro-pulsed radars for indicating the location of a body part to which the emitter is attached.

U.S. Pat. No. 7,011,660 to Sherman et al., discloses a brace installation instrument and method for the stabilization of bony structures. The installation instrument is a sextant-type tool with anchor extensions coupled to the anchors. The instrument is movable with respect to the anchors to position a brace in a position proximate to the anchors. The brace can be indexed for insertion at a predetermined orientation with respect to the installation instrument.

All of the aforementioned prior art disclose systems which utilize an implant insertion means to forcibly push the surgical implant or instruments to the target area in vivo. This increases the possibility of pathway divergence and/or damage to neural and vascular structures. What has been heretofore lacking in the prior art is a simple and economical system and procedure for the accurate and precise placement of surgical implants and/or instruments at a target area while providing a decreased risk to neural and vascular structures. Moreover, none of the aforementioned references provide audible and/or tactile feedback to the surgeon that indicates the target area has been reached.

SUMMARY OF THE INVENTION

The instant invention is related to a system suitable for guiding a biocompatible device, (implant, surgical instrument) to a target area within the body (in vivo), be it a tumor or implantation point for a fastening means. The system includes a targeting member which is attached to a tether. The tether and targeting member are preferably introduced to a target area through an introducer. The introducer, in accordance with the instant invention, includes a mechanism that winds and unwinds the tether allowing the attached targeting member to traverse a distance to the target area, thereby creating a pathway. The system further includes a second winding mechanism positioned at a distance from the introducer. Once the magnetic member reaches its final destination, the tether can be moved in a direction away from the introducer. Attachment of a biocompatible device to the tether allows the biocompatible device to be pulled through the tissue to put the device in place. The system also includes at least one anchoring member constructed and arranged to secure to a target area in vivo at one end.

Accordingly, it is an objective of the instant invention to provide a system that minimizes soft tissue damage and provides less post-operative pain.

It is a further objective of the instant invention to provide a targeting system that permits percutaneous positioning of a biocompatible device at multiple vertebral levels of greater than three.

It is yet another objective of the instant invention to provide a targeting system that can percutaneously treat scoliosis patients.

It is a still further objective of the invention to teach a targeting system which allows for shorter surgery, decreased x-ray exposure, and fewer complications for the patient.

It is a further objective of the instant invention to provide a targeting system that is simple to operate to reduce the training the surgeon must undergo for operation of peripheral systems.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 6 is the system shown in FIG. 1, illustrating the positioning of the targeting member within the magnetic introducer;

FIG. 7 is the system shown in FIG. 1, illustrating the release of targeting member from the magnetic introducer and traversal of the tissue space between vertebra thereby creating a pathway for the attached tether member;

FIG. 8 is the system shown in FIG. 1, illustrating the traversal of the magnetic introducer between vertebra along the path created by the targeting member and tether member;

DETAILED DESCRIPTION OF THE INVENTION

Figure 1:
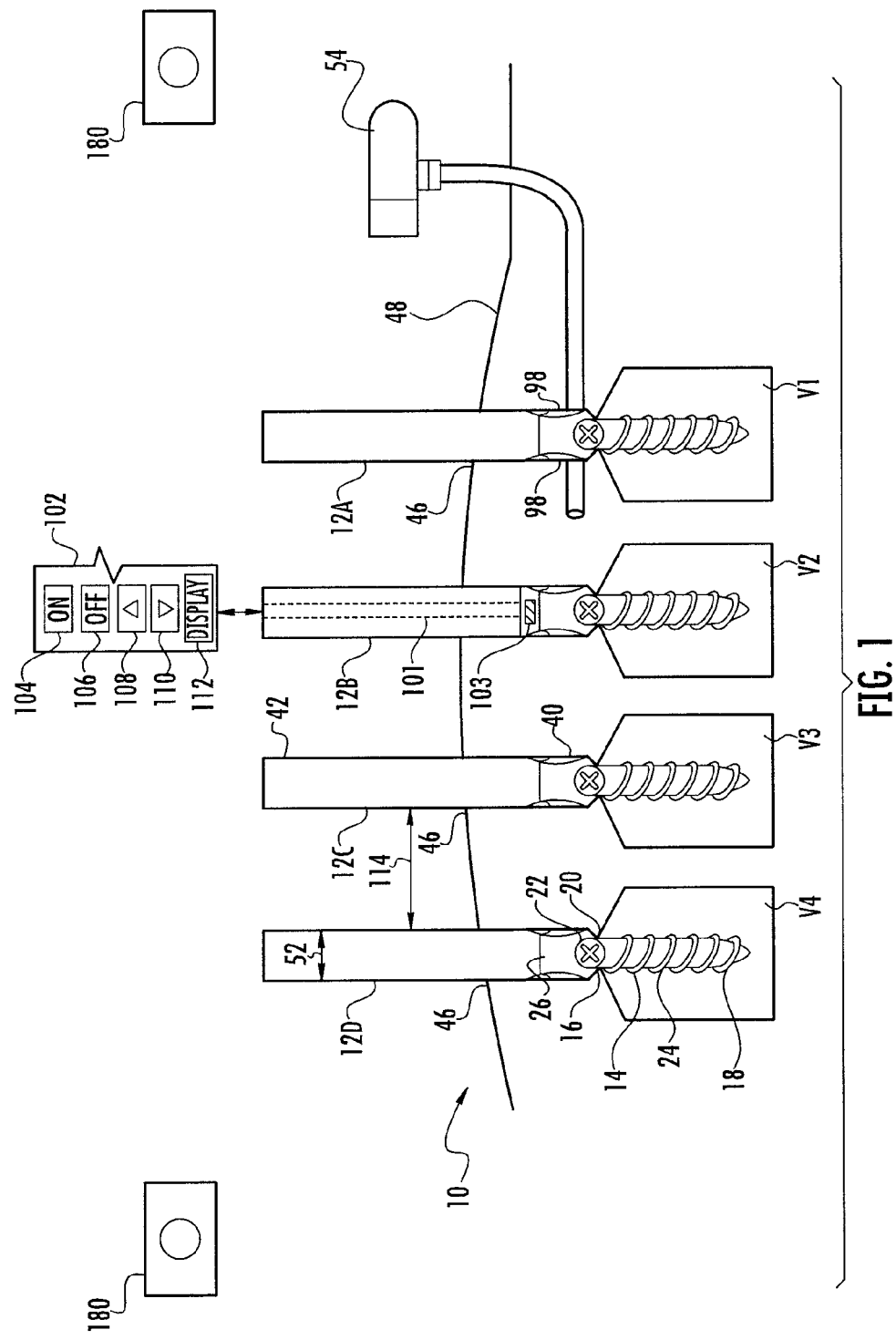
FIG. 1 illustrates a partial side view of a portion of a patient's spine which includes a suitable for pulling a biocompatible device to a target area located in vivo according to a preferred embodiment of the invention.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-8 which illustrate the system 10 of the present invention which is suitable for pulling and/or pushing implants in vivo via a tether, wherein like elements are numbered consistently throughout. FIG. 1 shows a plurality of extenders 12A, 12B, 12C, 12D, and collectively 12. The extenders 12 are shown having a generally tube or cylindrical shape, but may take on other forms. A plurality of anchoring members 14 (also referred to as fastening means) are used to secure the extenders 12 to one or more parts of a human body. The anchoring members 14 are depicted here as multi-axial pedicle screws, each removably attached to an extender 12A, 12B, 12C and 12D. The multi-axial pedicle screws have a proximal end 16 and a distal end 18. The proximal end 16 includes a head portion 20 with a tool opening 22 portion configured to receive a driving tool (not shown). The distal end 18 includes a threaded shank 24 designed to secure to a selected target area located inside the body of a patient (in vivo), shown here as consecutive spinal vertebrae V1, V2, V3, and V4. Although the target area is exemplified here as vertebrae in a partial spinal column, the target area may be located anywhere in vivo.

The screw shown here is a multi-axial screw where the proximal end of the screw may include a connector 26 rotatably connected to the head portion 20 of the screw. That is, the connector 26 is capable of 360 degree rotation relative to the threaded shank 24 of the screw along the axis L (see FIG. 9) of the shank. One example of a suitable multi-axial screw is described in U.S. Pat. No. 5,797,911, herein incorporated by reference. Although a multi-axis is exemplified herein, it is contemplated that a fixed axis screw may be used. Fixed-axis screws do not include a rotatable connector 26. Other means for anchoring are also contemplated herein, some of which include clamps, hooks, claws, bolts, or the like. Moreover, the shank of the anchor member may or may be not be cannulated, as is known in the art.

Figure 9:
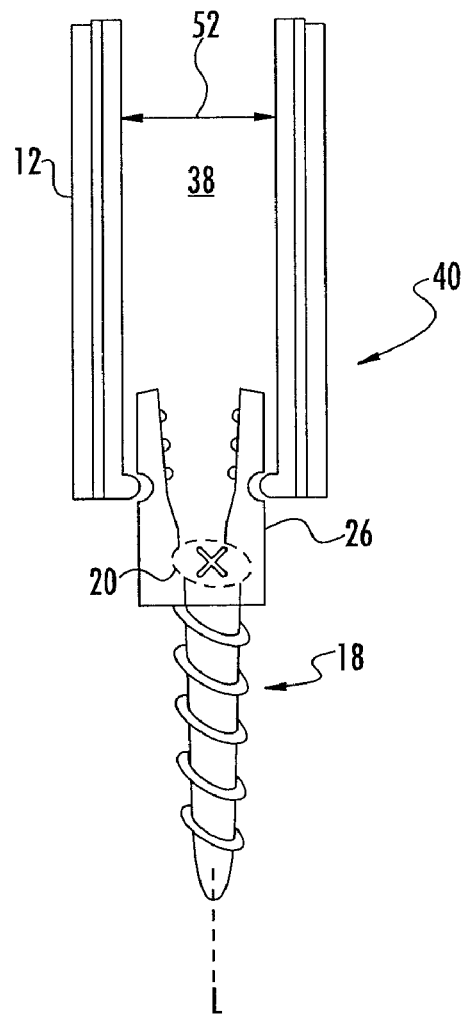
FIG. 9 is a partial cross-sectional view of a portion of the extender removably attached to the connector portion of the multi-axial screw in accordance with one embodiment.
Figure 10:
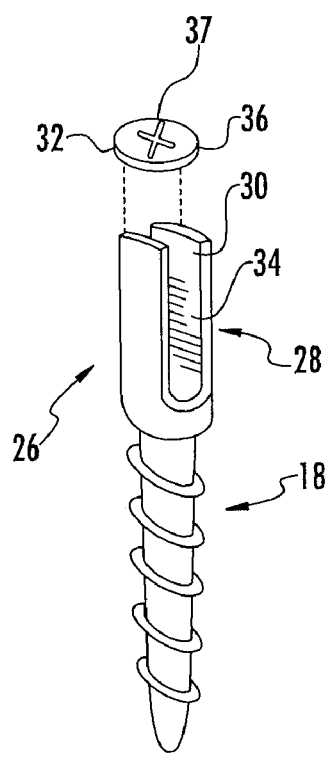
FIG. 10 is an upper perspective view of a multi-axial screw that can be used in the system of the present invention.

As shown in FIGS. 9 and 10, the connector portion of the screw is constructed and arranged to form a passageway 28 designed to removably receive implants of various sizes. The connector portion includes an opening 30 constructed and arranged to receive a set screw 32. As shown in FIG. 10, the connector portion includes threaded interior sidewalls 34 designed to mate with external threads 36 formed on the set screw 32. Thus, as the set screw is threadably lowered along the connector portion of the screw, the passageway 28 in the connector is narrowed. The passageway is narrowed until the exterior surfaces of a biocompatible device, such as an interconnecting rod 156, are sandwiched between the upper portion of the screw head 20 and the set screw 32. This acts to reliably secure the biocompatible device onto the screw. As with the head of the screw, there should be a tool opening 37 configured to receive a driving tool (not shown) inserted within the interior portion 38 of the extenders 12. The driving tool is well known in the surgical arts, and is used to rotatably secure the set screw to the desired position within the interior of the connector.

The distal end 40 of each of the hollow extenders 12A, 12B, and 12C is removably attached to the screws by any appropriate means known in the art. For example, the extender 12 may include a depressible member (not shown) located at the proximal end 42 of the extender that is operatively connected to an internal clamping member located at the distal end thereof. The clamping member is capable of engaging and disengaging the connector portion of the screw. One example of a suitable extender which could be used in the present invention is disclosed in U.S. Pat. No. 7,011,660, herein incorporated by reference. The extender may also be able to rotate the connector of a multi-axial screw relative to the shank to facilitate the threading of the interconnecting rod therethrough.

The extenders 12 should be made of a substantially rigid biocompatible material and have a length dimension that allows the proximal end 42 to protrude a distance outside of the percutaneous exposure 46 created through the outer skin 48 of the patient. The interior dimension 52 of the extenders 12 should be such that they are capable of receiving the appropriate driving tool (not shown) used to engage the screws and set screws. In addition, the interior dimension of the extenders should be able to accept a wand or other device for passing the targeting member and a tool, such as a magnet or gripping device for removing the targeting member to a location outside of the extender, as described further below. According to a preferred embodiment, the extenders 12 should have a "c-shape", as seen along an axis transverse its longitudinal axis, thereby defining a slot 98 that extends along its longitudinal axis and into the patient when attached to the screw. The slot should be sized to allow the targeting member to exit, so that it is able to be delivered percutaneously. Each of the proximal ends 42 of the extenders 12A-12D protrude outside of the patient's skin 48 through percutaneous incisions 46 so that the surgeon is able to insert instrumentation through the extender's interior portion to access the screw secured to the target area (vertebra). The extenders also enable the surgeon to insert the wand or removal tool into the selected extender to a position proximate the corresponding anchor 14.

Figure 12A:
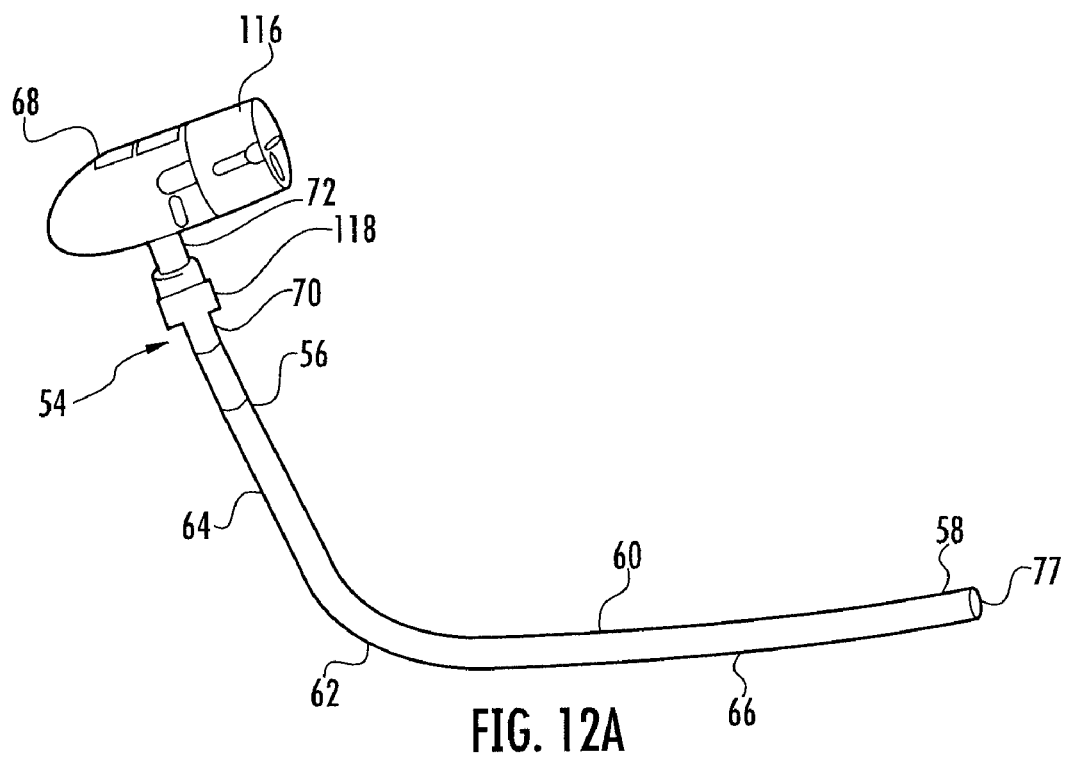
FIG. 12A is a perspective view of an illustrative example of the magnetic introducer that can be used in the system of the present invention.
Figure 12B:
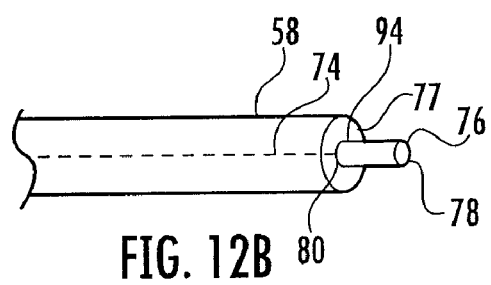
FIG. 12B is a partial view of the distal end of the magnetic introducer shown in FIG. 12A.

Referring back to FIGS. 1-8, a magnetic introducer 54 is used to introduce a targeting member into the system. The magnetic introducer 54 is constructed and arranged to deliver a targeting member to successive extruders 12 without the need for use of visualization techniques such as fluoroscopy. Referring to FIGS. 12A and 12B, an illustrative embodiment of the magnetic introducer 54 is shown. The magnetic introducer has a first end, or proximal end, 56, a second end, or distal end, 58, and an intermediate section 60 therebetween. The intermediate section may contain a bend 62 dividing the intermediate section into a generally vertical portion 64 and a generally horizontal portion 66. The intermediate section is made of a material that allows the user the ability to push the intermediate section 60 into place. Removably attached to the proximal end 56 is a handle 68. The handle 68 attaches to a connector 70 through a mateable connector 72 of the handle 68. Alternatively, the handle 68 may be integrally formed as part of the intermediate section. The handle 68 not only provides the user the ability to grab and manipulate the introducer through a space or tissue, but also stores the tether 74. A pre-determined length of the tether 74 is preferably wrapped around a winding/unwinding member, such as spool, not shown, in a similar manner as a fishing rod reel, so that the tether 74 may traverse the length of the intermediate section of the magnetic introducer 54. The opposite end of the tether 74 is attached to the targeting member 76. To provide such functionality, the introducer 54 is cannulated such that the targeting member 76 is movable through the distal end opening 77.

The targeting member 76 has a first end 78 and a second end 80. The first end 78 is designed to penetrate the tissue and is shaped to enlarge the opening while creating a pathway through the tissues as the targeting member 76 is advanced in vivo. At least the first end of the targeting member 76 may be composed of a steering material capable of being magnetically influenced, as described hereafter. Alternatively, the targeting member 76 can be made from any non-magnetically influenced biocompatible material.

Figure 11A:
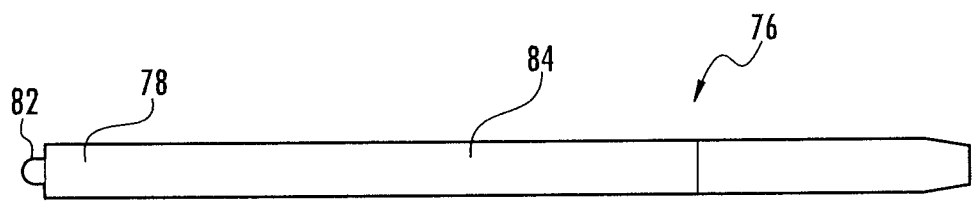
FIG. 11A is an illustrative embodiment of the targeting member that can be used in the system of the present invention.
Figure 11B:
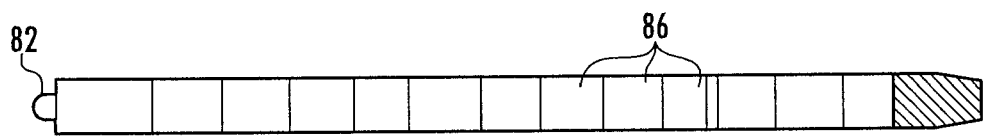
FIG. 11B is an alternative embodiment of the targeting member that can be used in the system of the present invention.
Figure 11C:
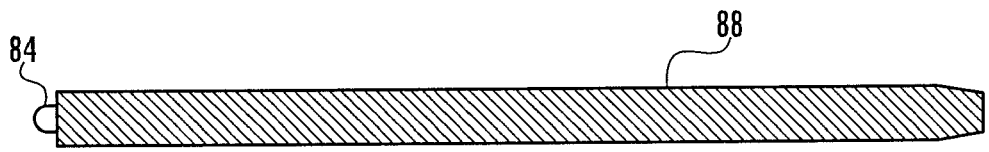
FIG. 11C is an alternative embodiment of the targeting member that can be used in the system of the present invention.
Figure 11D:
FIG. 11D is an alternative embodiment of the targeting member that can be used in the system of the present invention.
Figure 11E:
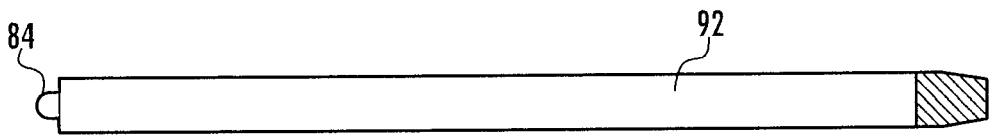
FIG. 11E is an alternative embodiment of the targeting member that can be used in the system of the present invention.

As shown in non-limiting embodiments, see FIGS. 11A-11E, the targeting member 76, which may be made from a flexible, semi-rigid, or rigid material, includes the steering material 82 located on the first end 78. FIG. 11A illustrates an embodiment of a semi-rigid targeting member in the form of a rod-like member with steering material 82 disposed on its first end 78. The first portion 78 of the rod is made of a flexible material capable of safely colliding with bony or neural obstructions without causing damage. FIG. 11B illustrates another flexible rod formed of a plurality of rigid consecutive segments 86 through which the tethering member 74 extends to the first end (not shown). When the surgeon pulls the tethering member at the second end taunt, the segments are forced together and little movement is permitted between the segments. In the embodiment of FIG. 11C, the entire targeting member is composed of or coated with a second biocompatible steering material 88. FIG. 11D illustrates another embodiment wherein the targeting member includes a ball joint 90 attached to the tethering member. As with the embodiment of FIG. 11B, the tension in the tethering member controls the amount of pivot at the ball joint. Thus, when tension is released the rod becomes flexible and the first end of the targeting member pivots on the ball. Alternatively, when the tension is reapplied to the tethering means, the rod is solid again. This way the surgeon is able to safely guide the targeting member around neural and bony obstructions as it moves through the body. Lastly, FIG. 11E depicts a rigid rod-like member formed from solid biocompatible material 92. Although not illustrated, the targeting member may be a magnet or magnetic material shaped in the form of a bullet.

The tethering member 74 may be made of any flexible or semi-flexible biocompatible material capable of allowing the device to navigate around neural and bony obstructions without damaging them. Examples of suitable tethering members may be in the form of a cable, cord or ligament. Moreover, the tethering member may be formed of a cannulated or solid member. The tether 74 should have sufficient tensile strength to pull the biocompatible device through said tissue pathway to said target area. As discussed above, the first end 94 of the tethering member 74 is attached to the second end 80 of the targeting member 76 by any means of attachment known in the art. Similarly, the second end 96 (not shown) of the tethering member is attached to the handle, through for example the winding/unwinding member (not shown), by any means of removable connection known in the art.

The steering material 82 in the targeting member 76, as used herein, refers to any material capable of being influenced by the magnetic material. For example, the steering material may include any magnetically attractive material or alloy, (e.g. steel, iron, etc). Moreover, the steering material may be coated with any suitable biocompatible element, such as plastic. The type, shape, and size of the magnetic material and steering material should be suitable for internal use in patients and provide the optimal magnetic field. Magnetic fields are used herein for navigating in vivo since these fields can penetrate human tissue and bone without being distorted similar to x-rays, but without the danger of radiation and physiologic damage.

Figure 2:
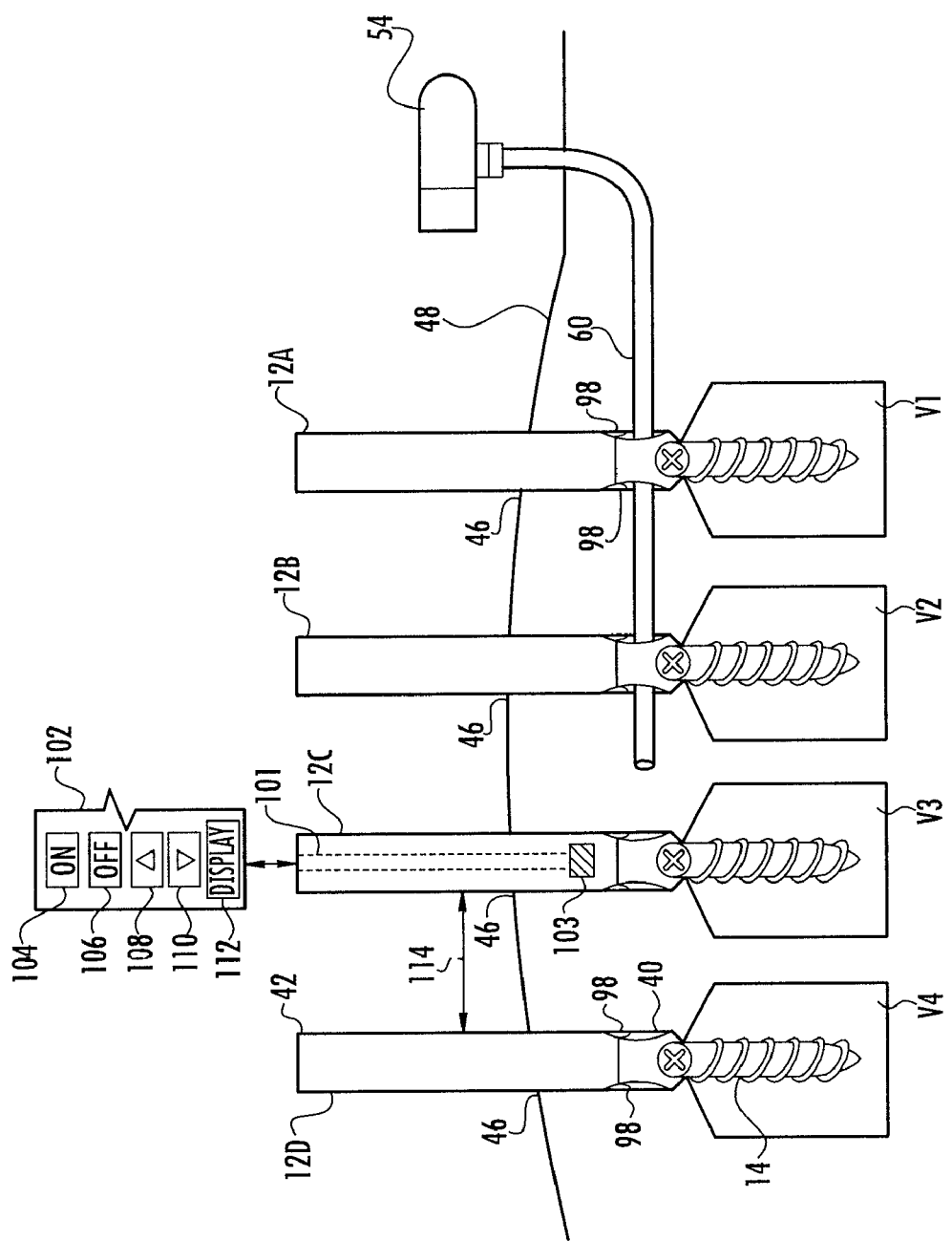
FIG. 2 is the system as shown in FIG. 1, illustrating the introducer with attached targeting member and tethering member threaded through an anchor member towards a retrieving device inserted located in an adjacent extender.
Figure 3:
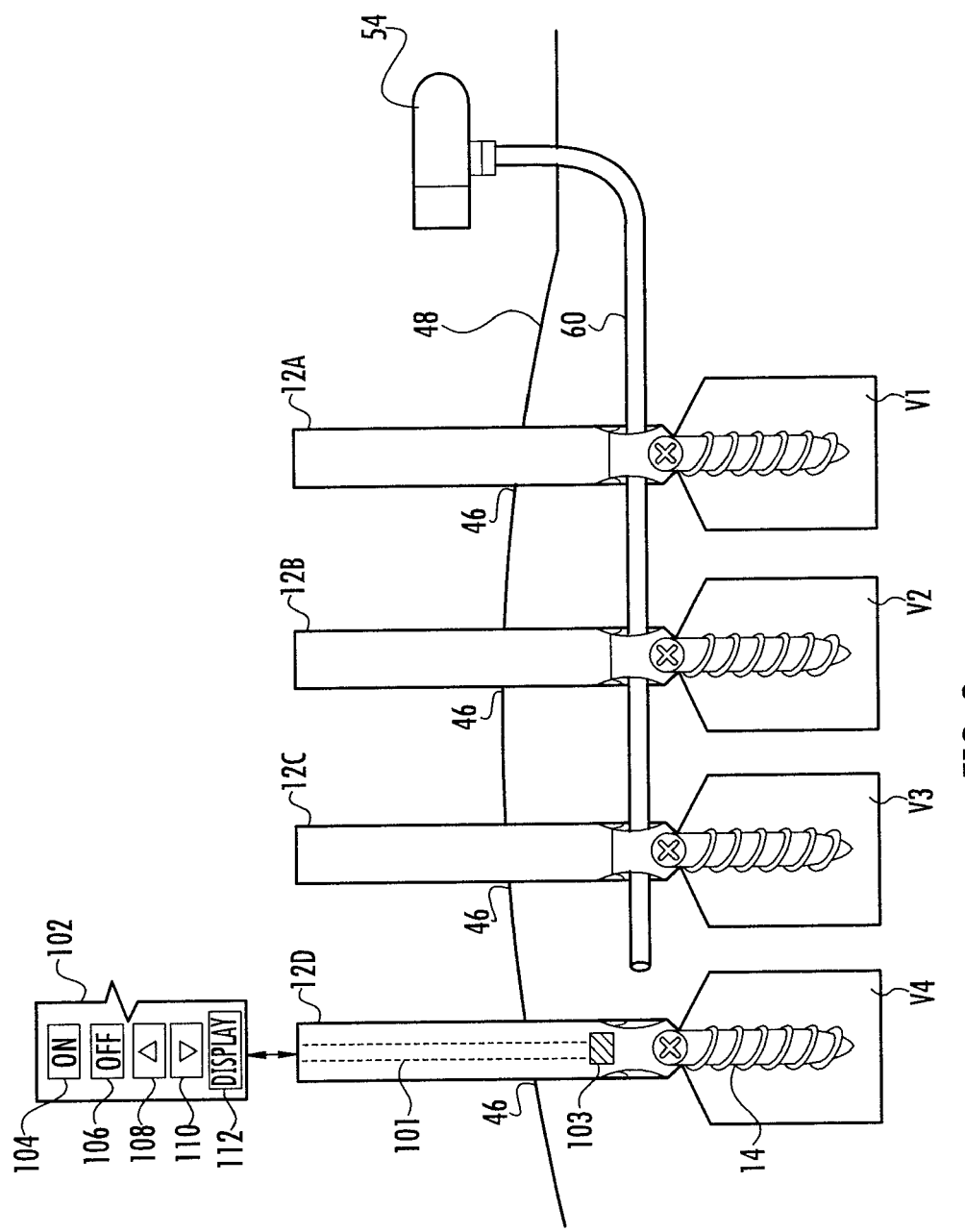
FIG. 3 is the system shown in FIG. 1, illustrating the magnetic introducer being moved between the patient's vertebra towards the last extender.

The magnetic introducer 54 is inserted into and through extender 12A via openings/slots 98 which are preferably designed to align with the passageway 28 of anchor member 14. As shown in FIG. 2, the magnetic introducer 54 may be inserted within and through the extender 12B. A magnetic device, such as a wand 101 having a magnetic material, such as a magnet 103, attached at the distal end thereto, and sized to extend the length of the extender, is placed within the extender 12C. Magnetic wands such as those described in U.S. Pat. No. 7,976,546, Publication Number US 2010-0234725 A1, or Publication Number US 2009-0082666 A1, and incorporated by reference, may be used. The magnetic wand 101 may be designed to employ an electromagnet having controls located in the handle or grip 102. At a minimum, the controls should include buttons and associated circuitry that will allow the surgeon to turn the electromagnet "on" 104 and "off" 106. Preferably, the controls also include buttons and circuitry capable of increasing 108 or decreasing 110 the strength of the magnetic field generated by the electromagnet and/or switch between polarity (north and south poles). As is known, the polarity of a magnet allows it to attract or repel magnetic material within its magnetic field. The controls can also include a display 112 used to indicate the strength of the magnetic field being applied.

Figure 4:
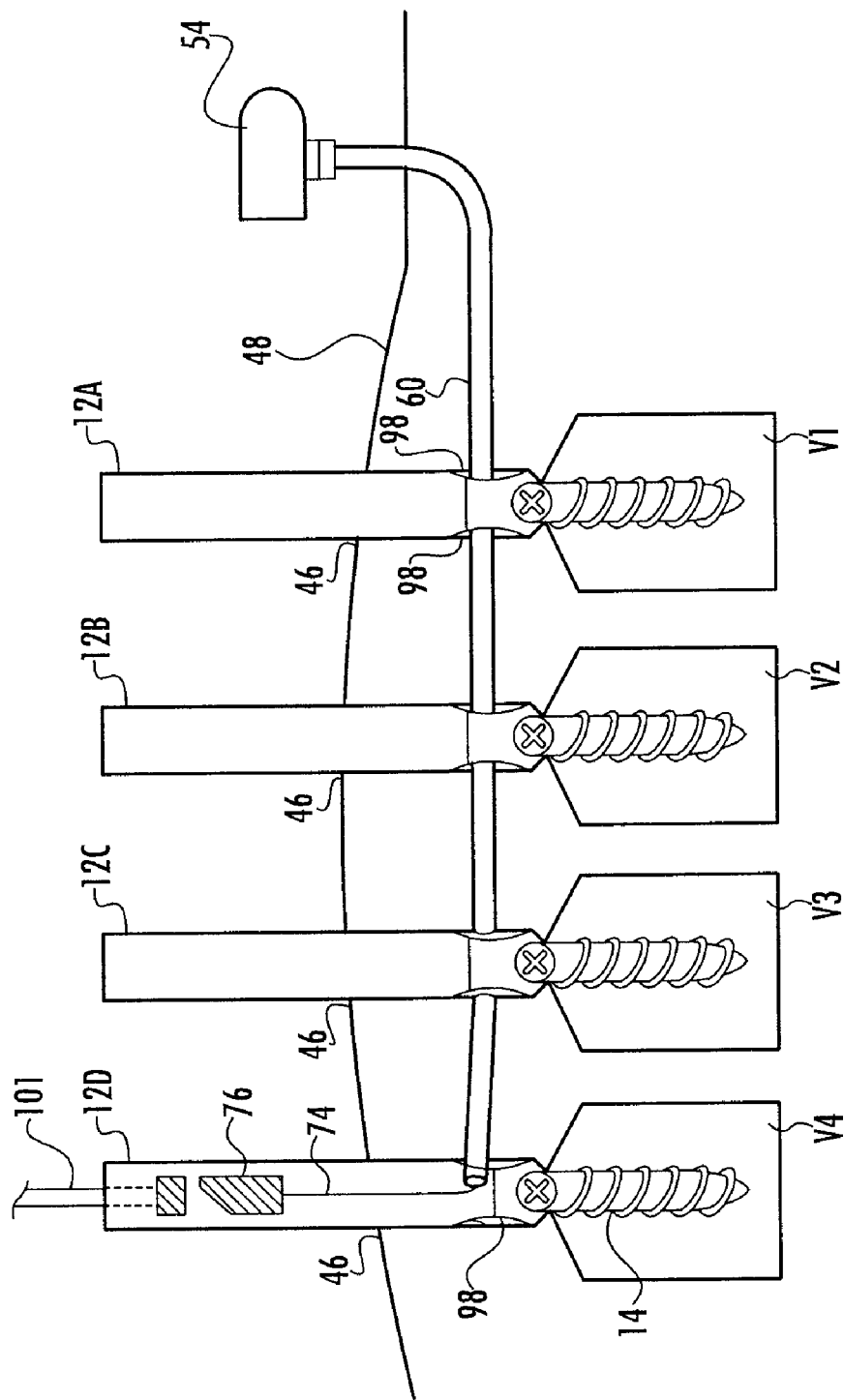
FIG. 4 is the system shown in FIG. 1, illustrating the targeting member being removed from the interior of the patient through the last extender.
Figure 5:
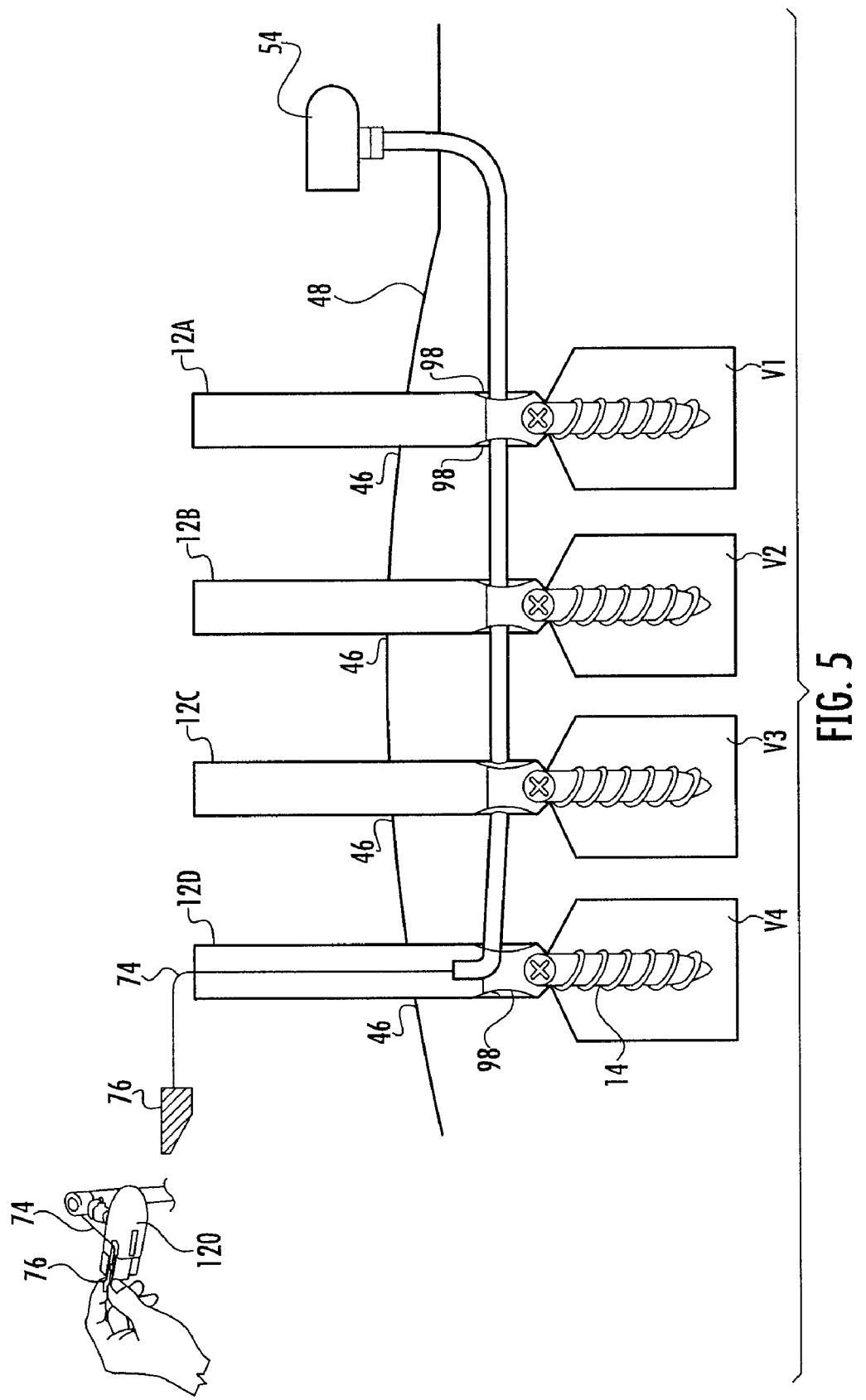
FIG. 5 is the system shown in FIG. 1, illustrating removal of the introducer and attachment of the targeting member to a cable winding device at one end and the tether member attached to a biocompatible device at the other end.

Insertion of the magnetic material 103 creates a the force that allows the targeting member 76, illustrated as a magnetic bullet, of the introducer 54 to traverse the space 114 between vertebra V3 and vertebra V4, entering the extender 12C through opening 98. As described previously, the targeting member 76 is attached to the tethering member 74. The tethering member 74 therefore, creates a path through the tissue space 114. In addition to the creation of the magnetic field through use of wand 101 which can be turned "on" and "off", the traversal of the targeting member 76 can be controlled through the amount of give and/or tension on the tether 74. For example, in a resting position, the tether 74 may be secured to the handle in such a manner that the targeting member 76 rests at or sticking out of the opening 77 of the distal end 58 of the introducer 54. Even if a magnetic field is applied, there is no slack on the tether 74 to allow the targeting member 76 to move. Turning the knob section 116 of handle 68 in a clockwise direction allows more of the tether 74 to be available so that, as the magnetic field is created, there is enough slack in the tether 74 to allow the targeting member 76 to move. Alternatively, or in addition to, the magnetic introducer may contain a nut 118 which allows the tether 76 to freely freespool, providing enough material for the targeting member 76 to reach its destination. Once the targeting member 76 reaches its destination, the knob 116 can be turned in a counter-clockwise direction to tighten, or the knob 116 can be turned in a counter-clockwise manner. Since the targeting member 76 is securely coupled to the magnet 103 of the wand 101, the intermediate section 60 of the magnetic introducer 54 traverses the path created by the tether and secures to the extender 12C through opening 98, see FIG. 2. The same steps are then repeated until the final vertebra is reached, see FIGS. 3-4. Referring specifically to FIG. 4, once the magnetic introducer 54 reaches its final destination V4, the tether member 74 can be released so that it may be retrieved and pulled upwardly by the magnetic wand 101, allowing the targeting member 76 to be lifted out of extender 12D. The magnetic member 76 can then be attached to a tether winding device 120 which is used to traverse one or more implants along the path created by the tether 74 as described later.

Figure 13:
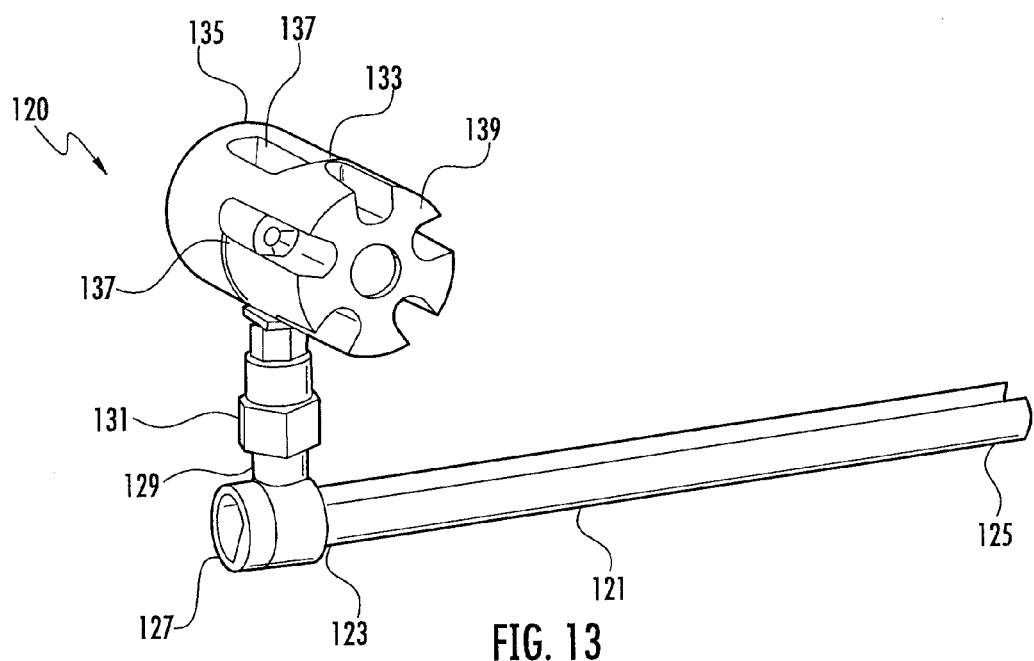
FIG. 13 is a perspective view of an illustrative example of a cable winding device that can be used in the system of the present invention.

Referring to an illustrative embodiment of the tether winding device 120 shown in FIG. 13, the cable winding device 120 contains a cannulated tube 121 having a proximal end 123 and a distal end 125. The distal end 125 preferably contains one or more slotted portions (not shown). The proximal end 123 contains opening 127. The opening 127 allows the user the ability to insert one or more surgical devices, such as a retrieval device, into the interior of the cannulated tube 121 to receive the target member 76 and pull it up from the distal end 125. Along the side of the tube 121, near the proximal end 123, is a first connecting member 129 which is mateable with a second connecting member 131. The second connecting member 131 connects a tether winder 133 to the cannulated tube 121. The tether winder 133 contains a main body 135 which is constructed and arranged to receive and store the targeting member 74 and tether 74 within. The tether winder main body may contain one or more slotted portions 137 sized and shaped to receive the targeting member 76. Once placed inside the slotted portion 137, the targeting member may be aligned with a device, such as tether winder reel which allows the user to turn a rotatable knob 139 to wind the targeting member 76 and tether 74 around the reel. Alternatively, the tether may simply wind around the tether winder main body or the knob 139. The tether winder 133 may further be designed to have ratchet means such turning the knob one revolution at a time in one direction (clockwise) and/or turning the knob one revolution at a time in the opposite direction (counterclockwise) to unwind prevents the unwanted winding and/or unwinding. The tether winder 133 may also be designed to allow the tether to wind/unwind freely without restriction. The cannulated tube 121 may additionally contain a wheel (s Figure bar, a pin, a wheel located at the distal end 125, to limit or prevent unwanted movement of the tether, thereby preventing the tether 74 from moving upwardly, towards the proximal end when being tightened or wound.

Figure 14A:
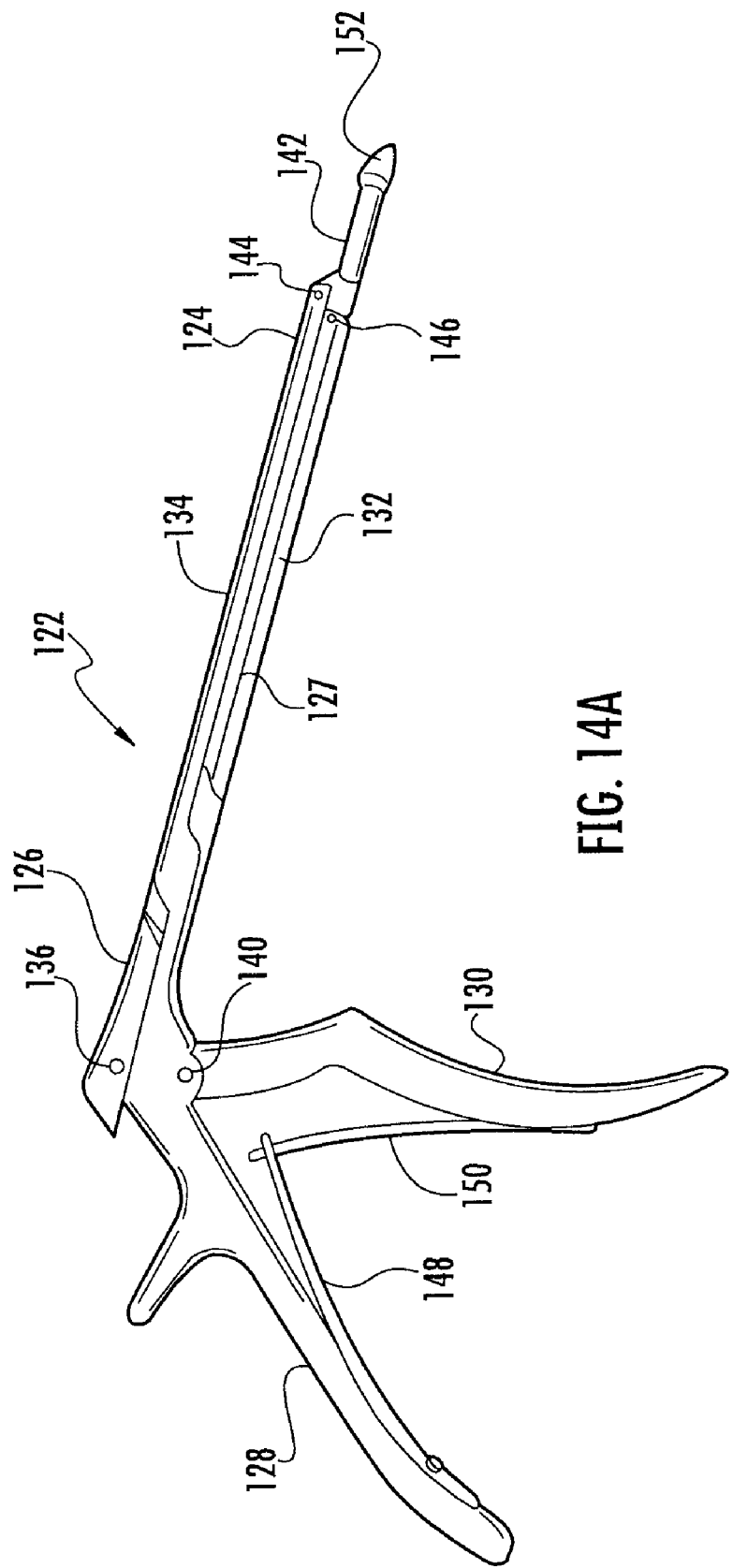
FIG. 14A is a perspective view of the passing device that includes the passing member for the targeting member.

Referring to an alternative embodiment shown in FIGS. 16-23, the system suitable for pulling a targeting device to a treatment area in vivo 10 of the present invention may include the use of one or more passer devices to aid in the placement of one or more implants without the need of fluoroscopy. Similar to the system described previously, the placement of the implants is provided by using a magnetic field or other means that pulls the biocompatible device along a path created by a targeting member, thereby reducing the probability of damaging or breaking obstructions encountered along its path. The system 10 illustrated in FIGS. 16-23 utilizes many of the same components as described above. The magnetic introducer 54 is inserted into and through the extruder 12A through opening or slot 98 so that the distal end of the intermediate portion 60 rests at or near the opening/slot 98 of extender 12B. A first retrieval device 155 or passer device 122 is inserted into an adjacent extender 12C, see FIG. 17. FIGS. 14A-14D show illustrative embodiments of the retrieval and/or passer devices. Referring to FIG. 14A, the passer device 122 contains a distal end 124, a proximal end 126, and a main body 127 there between. At the proximal end 126 is a hand holding grip 128 and a trigger-like component 130 pivotally attached thereto. The main body 128 may comprise a first elongate rod-like member 132 and a second rod-like member 134 positioned adjacent the first rod-like member 132. The second rod-like member 134 is hingedly connected to the trigger 130 through pivots 136 and 140 at one end, and hingedly connected to a passer member 142 via pivot 144 at the opposite or distal end 124. The passer member 142 is pivotally connected to the first rod-like member 132 at pivot 146. Cantilevered flat springs 148 and 150 are positioned to bias the hand grip 128 and trigger 130 away from one another absent a force exerted by the operator's hand.

Figure 14B:
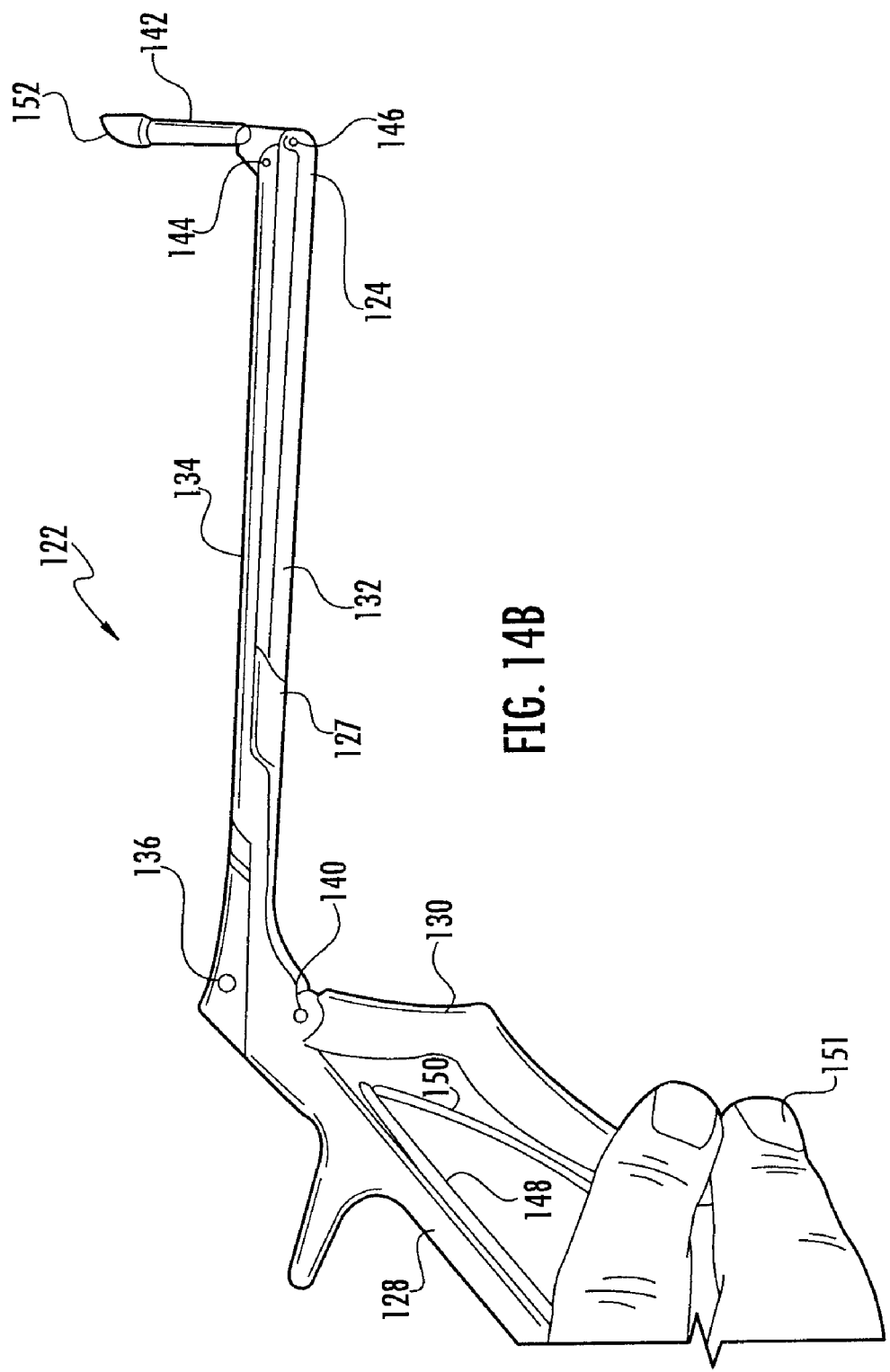
FIG. 14B is a perspective view of the passing device shown in FIG. 14A with the passing member in a raised position.

In operation, the operator's fingers 151 will grip trigger member 130 and pivotally move in towards the hand grip 128, see FIG. 14B. When springs 148 and 150 abut the trigger and the hand grip, they will act against the force exerted by the operator's fingers 151. The pivotal motion of trigger 130 relative to hand grip 128 will result in the relative axial displacement of the first rod-like member 132 with respect to second rod-like member 134. The relative displacement will result in the pivotal movement of passer member 142, as shown in FIG. 14B, via the displacement of pivot 146 with respect to pivot 144. The passer device 122, including passer member 142, is sized to fit within the internal cavity of extenders 12.

Figure 14C:
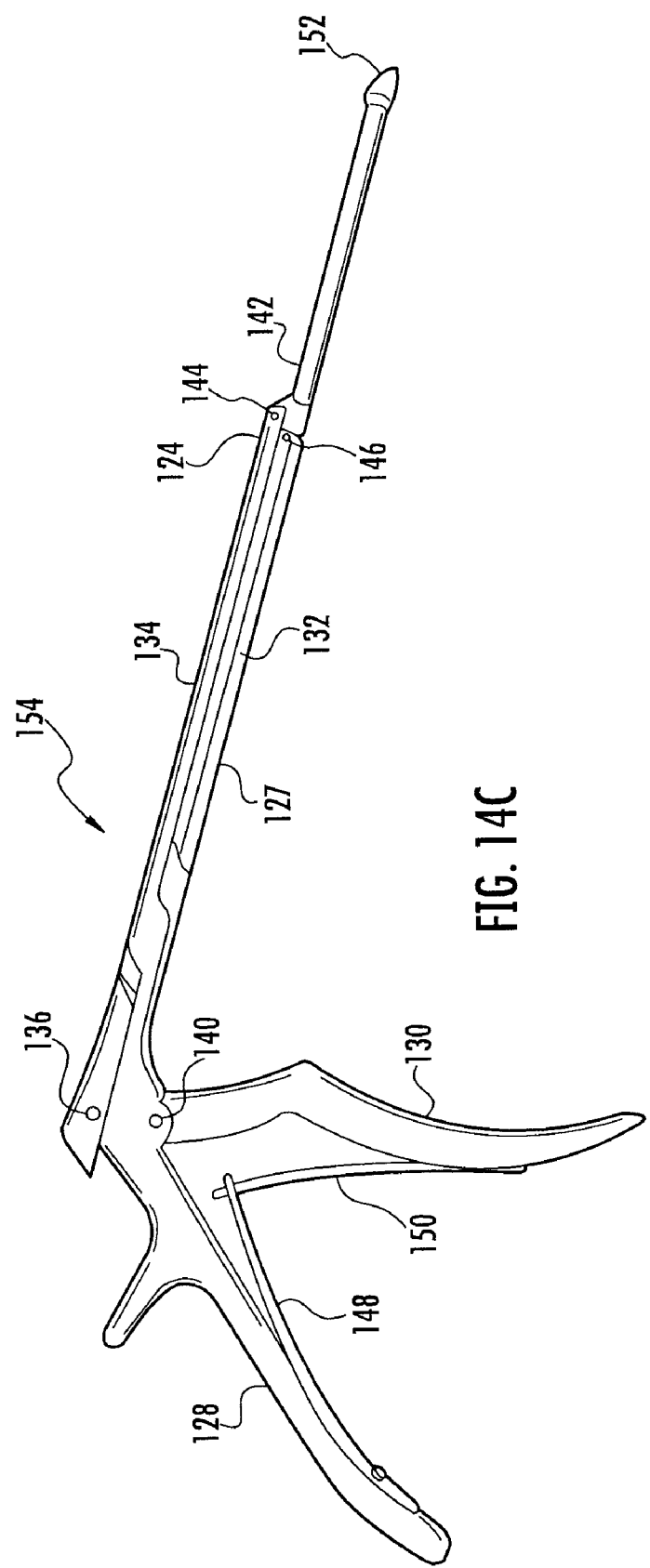
FIG. 14C is an alternative embodiment of the passing device shown in FIG. 14A.
Figure 14D:
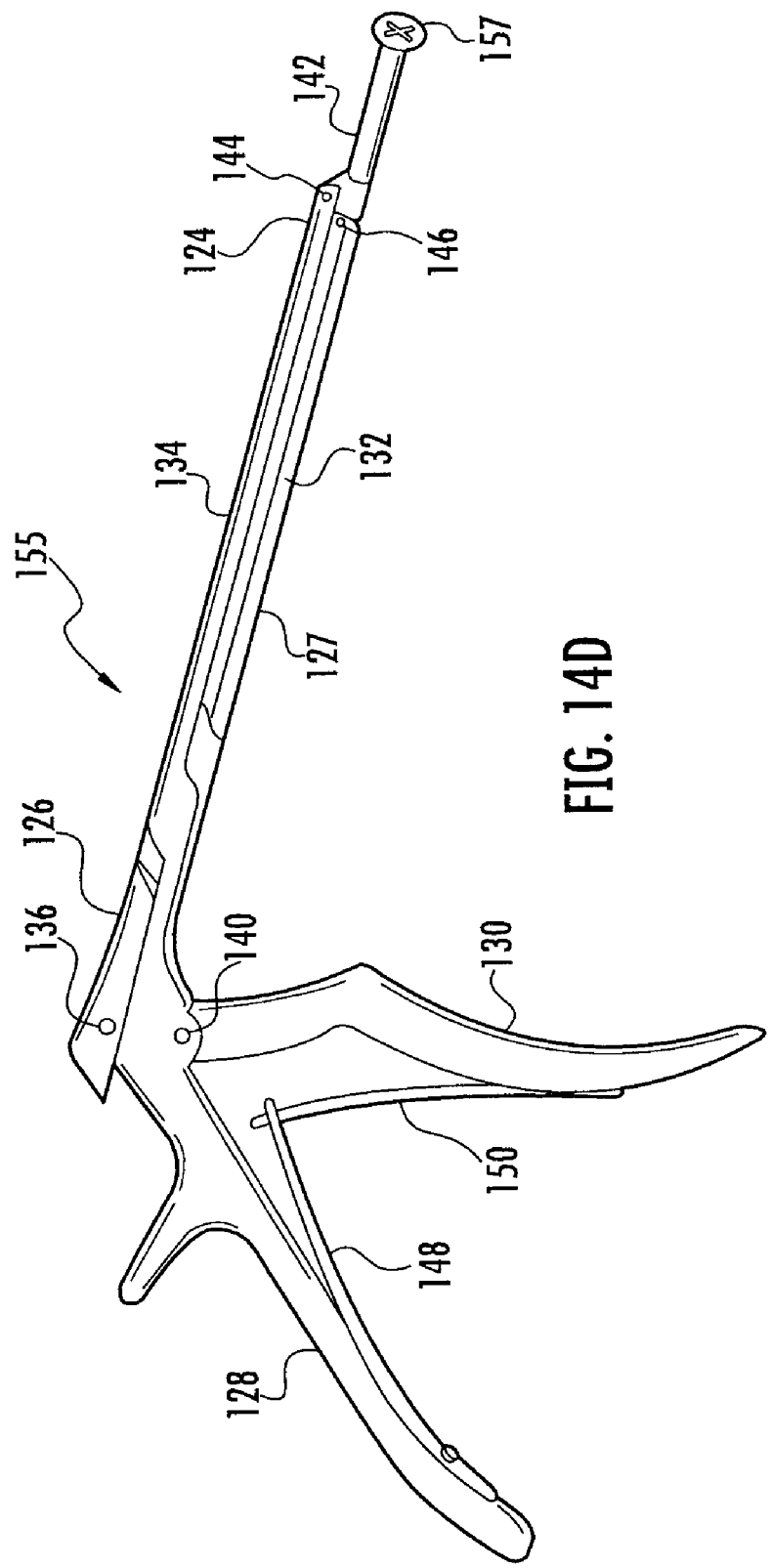
FIG. 14D is an alternative embodiment of the passing device shown in FIG. 14A.

The passer member 142 includes a cavity 152 formed at its distal end which is sized and configured to receive and secure the targeting member 76. FIG. 14C illustrates a second passer device 154 having an elongated passer member 142. Both the first passer 122 and the second passer 152 may alternatively include claw-like structures which are in operative engagement with the grip 128 and the trigger 130 so that engagement of the trigger 130 results in the claw-like structures moving towards each other. In this configuration, the passer device can be used to grab and hold the targeting member 76. The passer devices may also be adapted to act as a retrieval device by replacing the cavity 152 on the passer member 142 with a magnetic catch, such as a magnet 157, designed to attract and firmly secure the targeting member 76 to the passer member 142, see FIG. 14D.

Figure 15A:
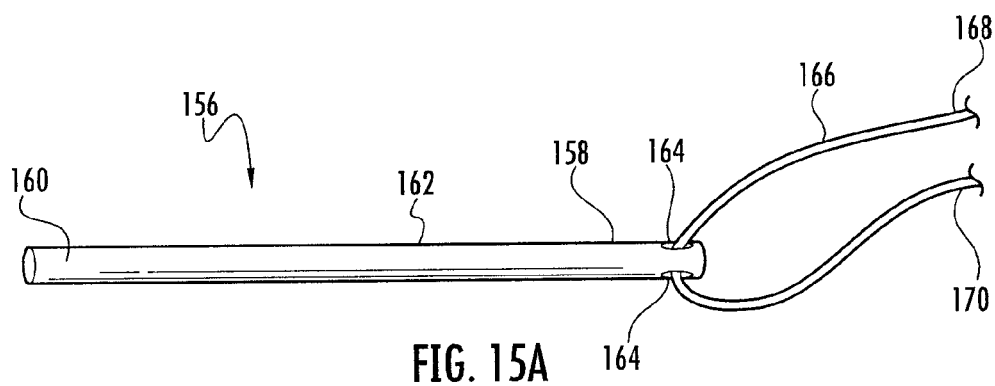
FIG. 15A is an illustrative embodiment of a biocompatible device that can be used in the system of the present invention shown attached to a cable.

The present system further includes one or more biocompatible members, such as but not limited to spinal implants including plates, rods, hooks, which when attached to the previously positioned tether 74 can be guided to placement and securing to the anchoring members 14. Referring to FIG. 15A, an example of a biocompatible member, illustrated herein as an interconnecting rod 156, is shown. The rod 156 may be rigid, semi-rigid or flexible. Rigid rods are usually preferred for providing the necessary stability during the healing process and arthrodesis, however, flexible rods have been found to provide for arthrodesis while allowing some movement between bony structures that have been interconnected to preserve some motion. Moreover, like the tether 74, the biocompatible device may also be solid or cannulated. The rod member 156 contains a first end 158, a second end 160, and an intermediate portion 162. The first end 158 is constructed to penetrate and travel through the pathway created by tether 74. The first end also contains a connecting mechanism, illustrated herein as eyelets 164, for coupling a cable 166 to the rod 156. The first end 168 of the cable 166 connects to a second end 170 of the cable 166 at a first end 172 of a crimp sleeve 174. The second end 176 of the crimp sleeve 174 is constructed and arranged to couple the tether 74 to the cable 166. Such an arrangement effectively couples the rod member 156 to the tether member 74 so that moving the tether 74 moves the rod 156 into place by allowing the rod 156 to be pushed through an already created pathway to the target area in vivo. The first end 158 may also contain a breakaway portion for easy removal of the connecting mechanism. The rod may also be connected to the tether 74 through corresponding threads that the surgeon can rotate to disconnect the tether 74 from the rod 156. The body portion 162 of the rod 156 is constructed and arranged for attachment to a target area, such as pedicel screws, in vivo.

Although the interconnecting rod is shown in FIGS. 16-23 as interconnecting 5 pedicle screws, the surgeon could use any appropriately sized rod having a length dimension capable of interconnecting three or more fastening means co-linearly implanted along multiple vertebrae. It is also within the purview of the invention that any sized rod having various widths or diameters could be used so long as it is capable of stabilizing the bony structures for bony fusion. Although a rod-like member is exemplified herein, other such biocompatible devices known to one skilled in the art are also contemplated, for example, plates, clamps, hooks, etc.

The method of using the system 10 of the present invention is described in accordance with the embodiment depicted in FIGS. 16-23. First, the anchoring members 14 (shown here as the multi-axial pedicle screws) are inserted into the desired target area (shown here as vertebra V1-V5), as is known in the surgical art, and may include such instruments as insulators, dilators, ratchet handles, and drivers. The screw may be removably attached to the distal end of the extender 12 before or after attachment of the screw to the selected vertebrae. Once the extenders 12A-12E are attached to the corresponding vertebra V1-V5, the surgeon inserts the introducer 54 so that the distal end 58 is inserted into the proximal end of the extender 12A which protrudes outside of the percutaneous exposure 46. The introducer 54 is loaded with the targeting member 76, preferably positioned at or near the distal end, attached to tether 74. The second end of the tether 74 is coupled to the winding/unwinding mechanism of the handle 68. The distal end 58 of the introducer 54 is inserted within the extender 12A through opening/slot 98 and is pushed through the tissue space 114 to create a pathway.

Once the introducer 54 is at or near the opening 98 of the adjacent extender 12B, the surgeon either rotates the knob 116 of the handle 68 on the introducer 54 or releases the nut 118 in order to loosen the taut tether 74. The loosened tether allows the targeting member 76, which is resting at the distal end of the introducer 54, to move freely. The surgeon places a recovery instrument, such as the wand devices described previously, or the retrieval instrument 155 into the internal space 52 of the extender 12C. The surgeon exerts pressure on 128 and 130 to cause the passer portion 142 with magnetic catch 157 to extend into the tissue space or align at, or near the opening/slot 98 of the distal end of the extender 12C. In either case, the targeting member 76, illustrated as a magnetic bullet, is drawn to the magnetic catch 157, traversing the distance 114 between V2 and V3. As the targeting member 76 moves towards the direction of extender 12C, a pathway is created and the tether 74, which is attached to the targeting member 76, moves as well. The surgeon releases the pressure on 128 and 130, causing the passer member 142 to retract back, thereby allowing the surgeon to remove the retrieval instrument 155 up through the internal space 52 and out of the extender 12C.

Figure 18:
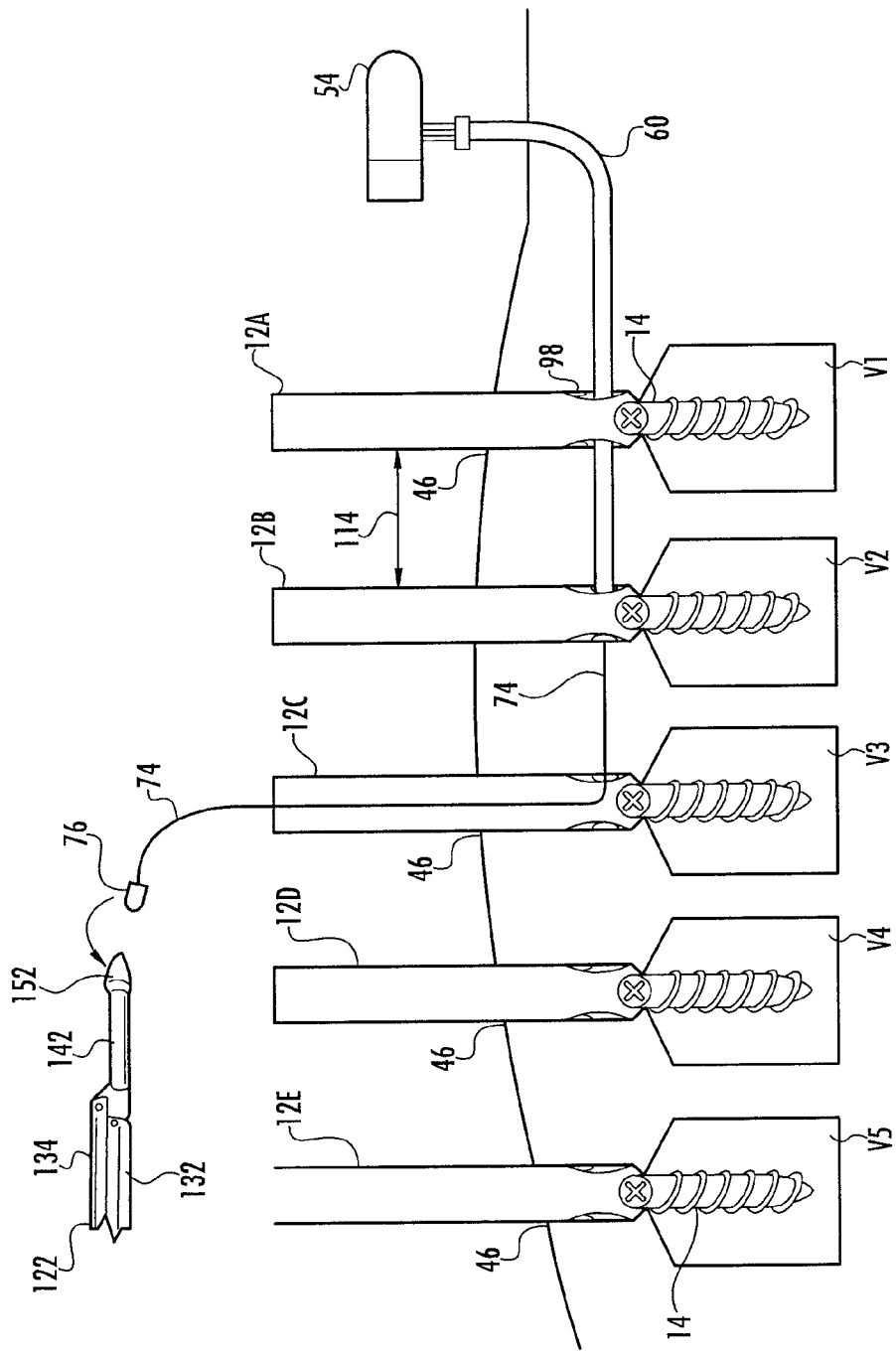
FIG. 18 is the system as shown in FIG. 16, illustrating the coupling of the targeting member to the passing device.
Figure 19:
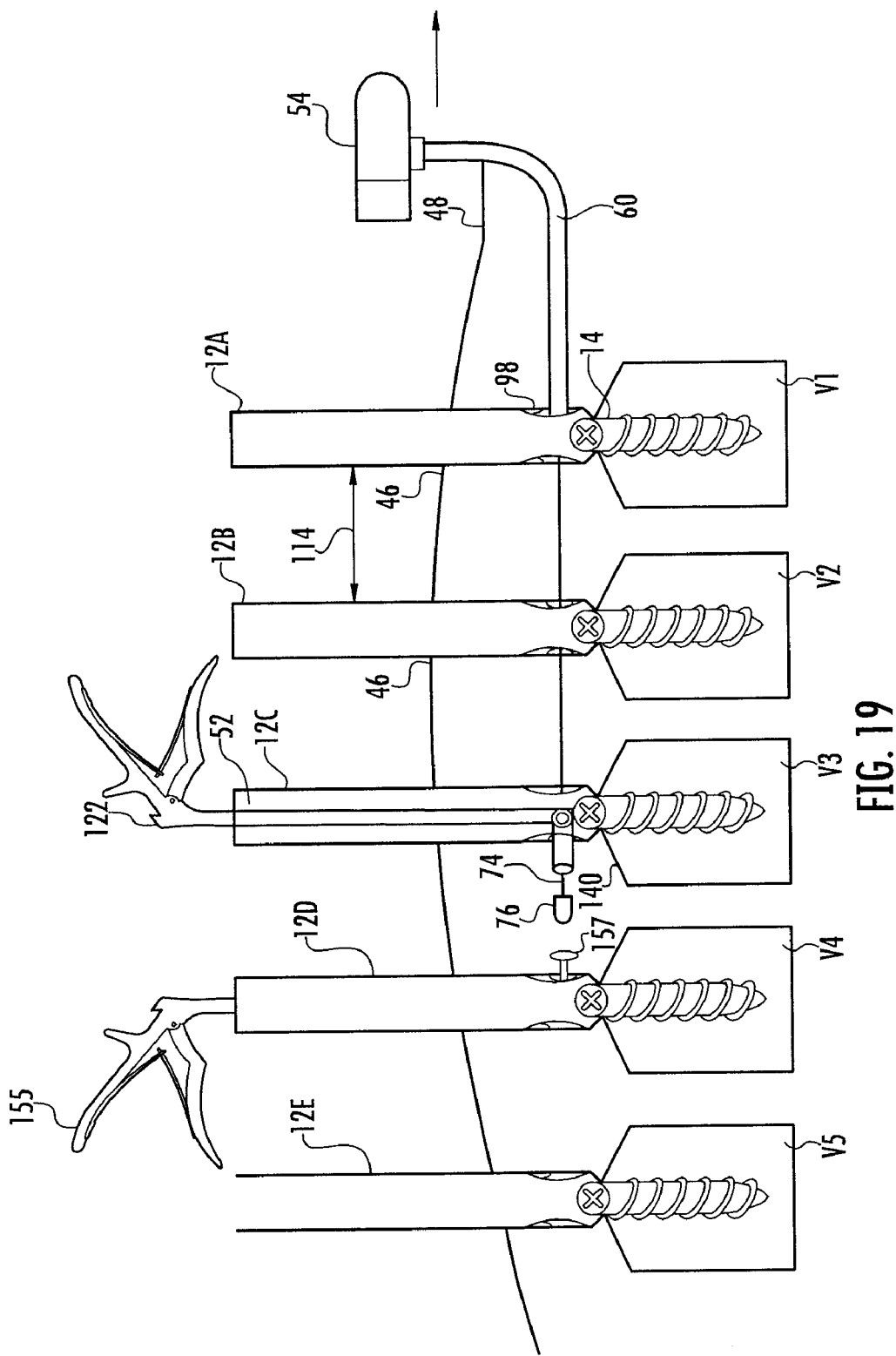
FIG. 19 is the system as shown in FIG. 16, illustrating the insertion of a passing device within an extender and the insertion of a retrieving device within an adjacent extender.
Figure 20:
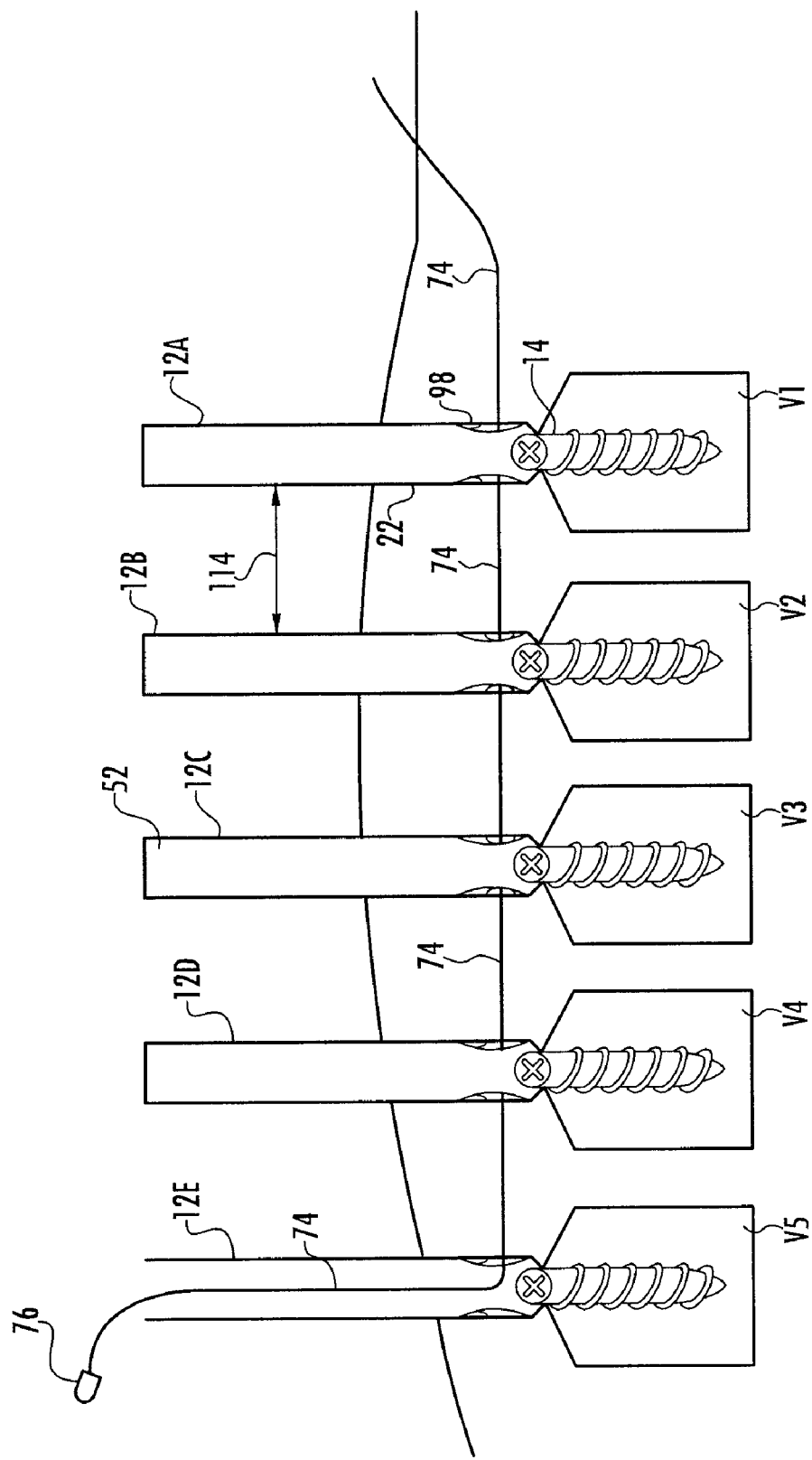
FIG. 20 is the system as shown in FIG. 16, illustrating the targeting member inserted up into and through the final extender.
Figure 21:
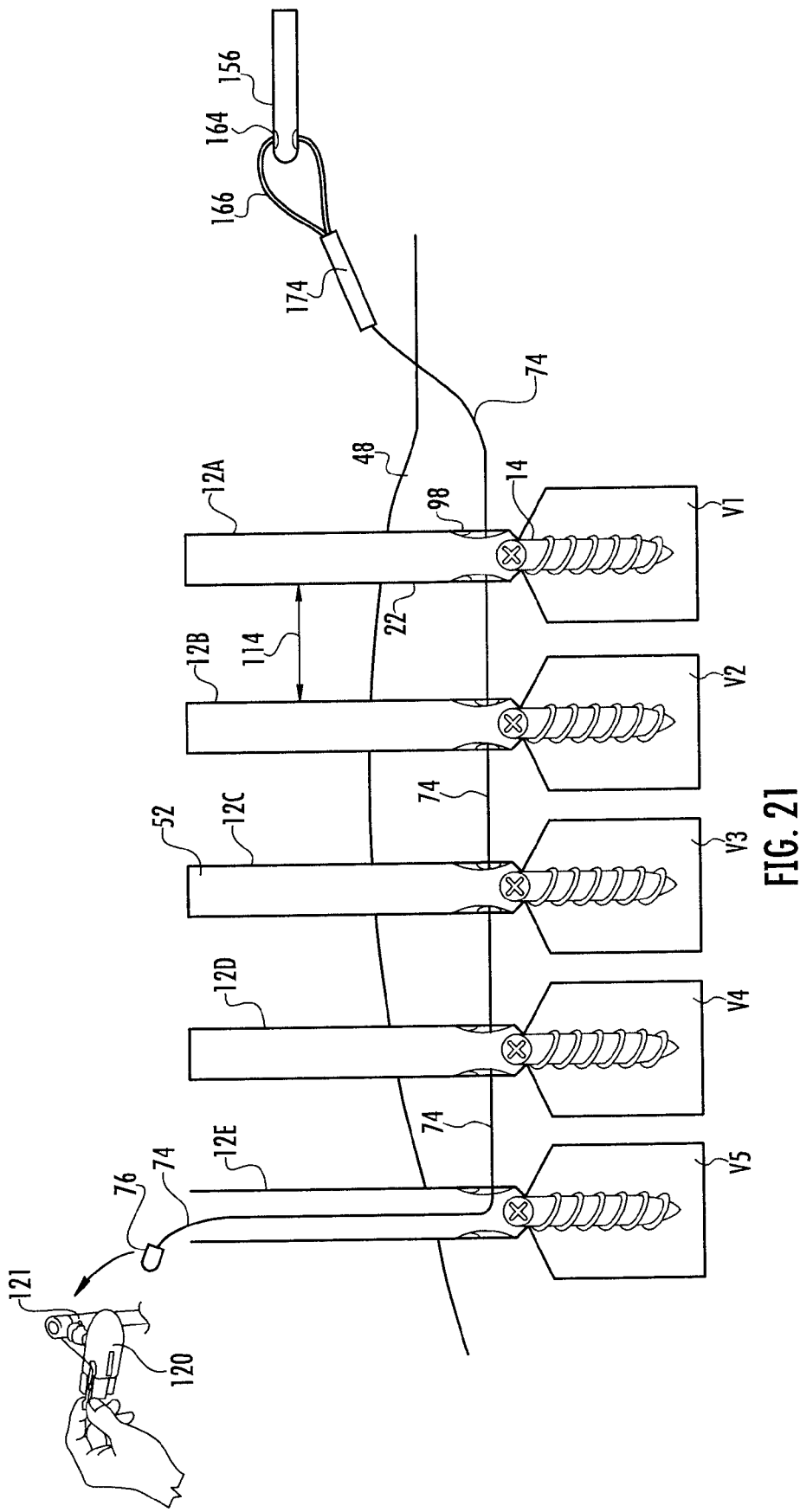
FIG. 21 is the system as shown in FIG. 16, illustrating the coupling of the targeting member/tether to the cable winding device and the coupling of the tether to a biocompatible device at the opposite end.
Figure 22:
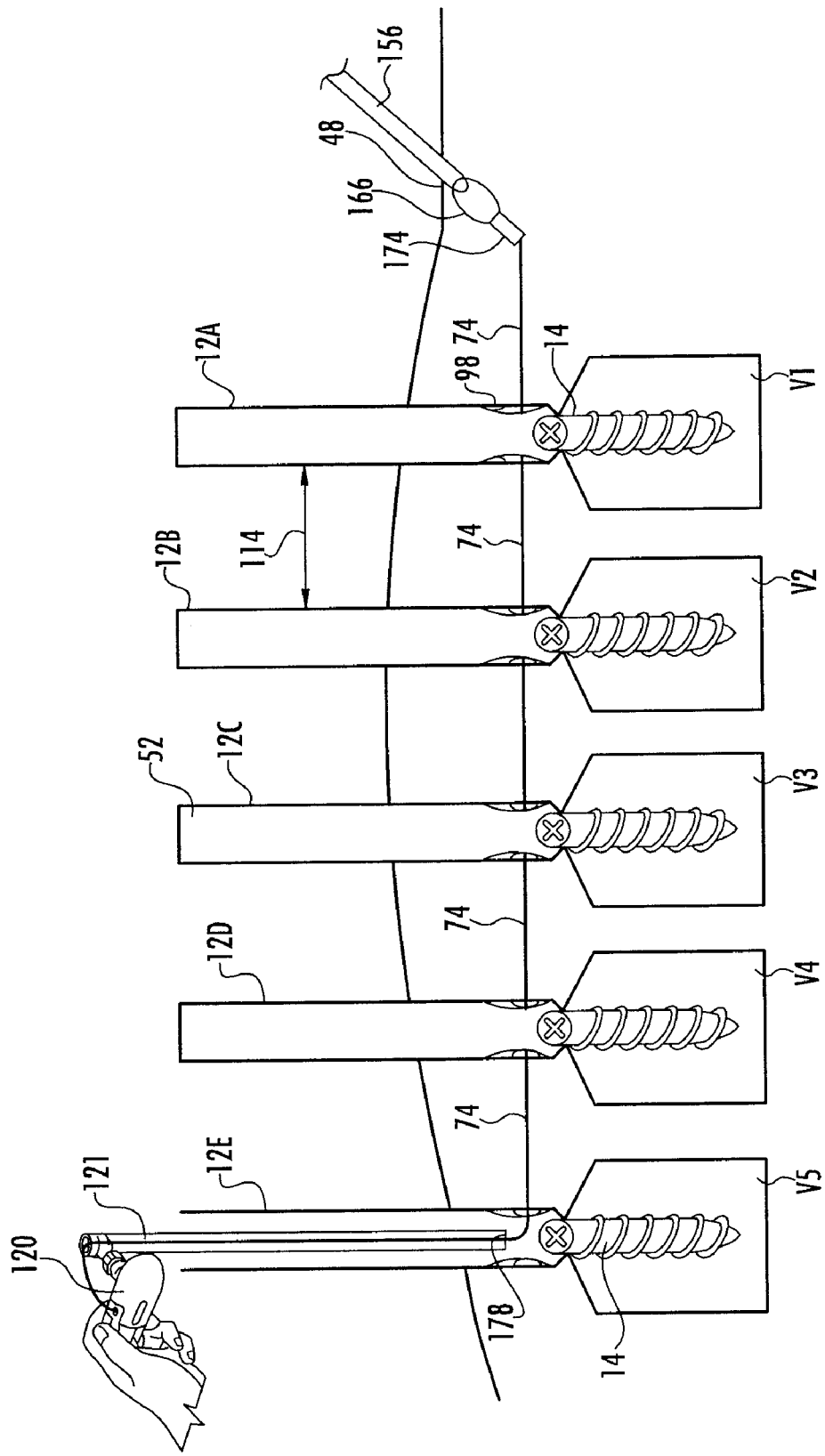
FIG. 22 is the targeting system as shown in FIG. 16, illustrating the biocompatible device being pulled into the treatment area within the body of the patient.
Figure 23:
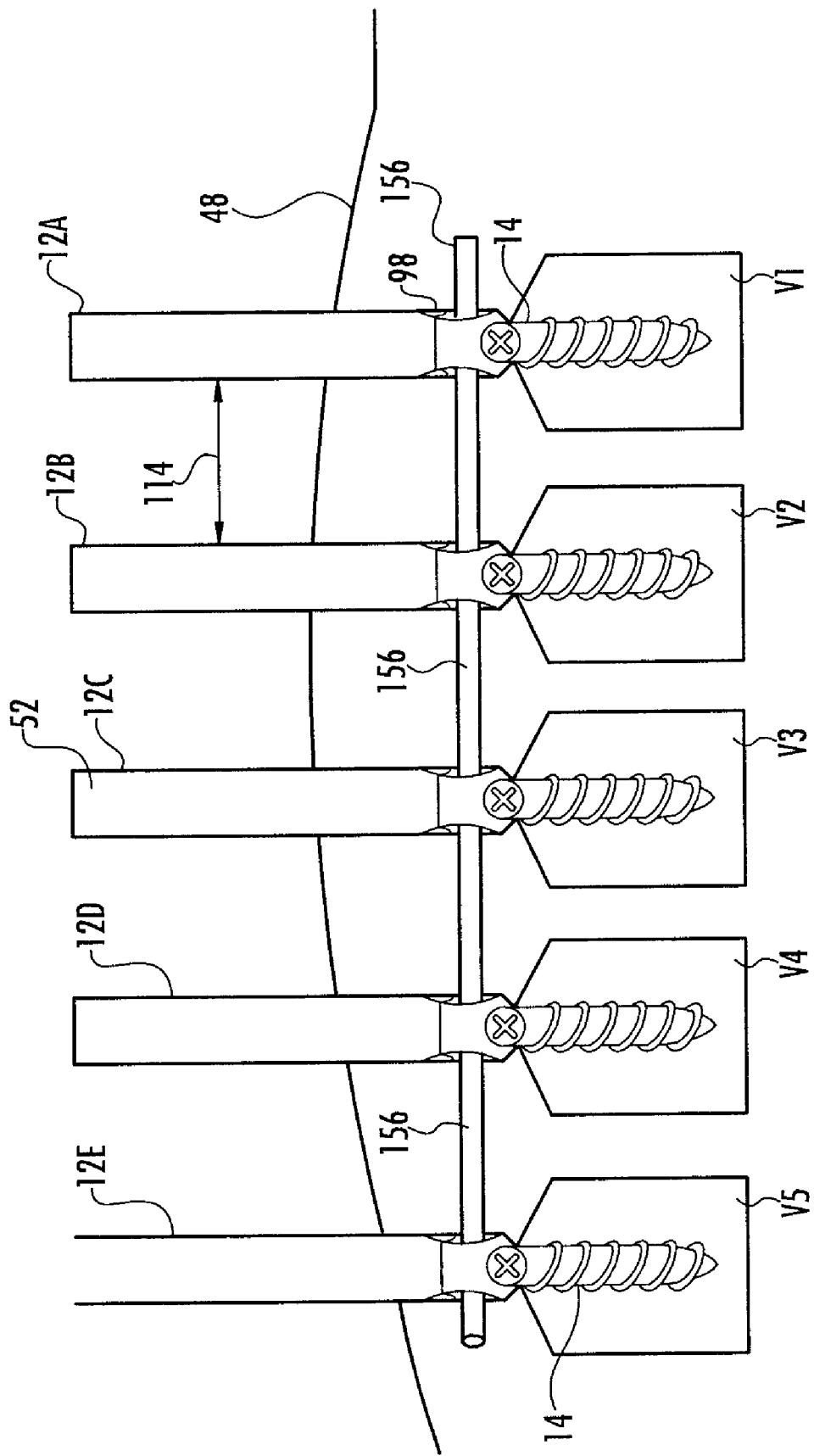
FIG. 23 is the targeting system as shown in FIG. 16, illustrating the biocompatible device resting on and secured to the treatment area within the body.

Once the retrieval instrument 155 is removed from the extender, the targeting member 76 is removed from the catch member 157 and inserted into the cavity 152 of the passer 122 or 154, depending on the length desired, see FIG. 18. Once secured, the passer device 122 is placed back into the internal space 52 of the extender 12C, see FIG. 19. The targeting member 76 is then directed to the adjacent extender 12D. Using either a second passer or the retrieval instrument, the targeting member 76 is directed towards the extender 12D by repeating the previous steps. The targeting member 76 is further moved to additional extenders 12 by repeating the steps outlined above. Once the targeting member 76 reaches the final extender 12E, the retrieval device 155 or the passer device 122 is pulled up through the extender, see FIG. 20. The targeting member 76 is inserted through the tether winder tube 121. The surgeon then inserts the targeting member 76 into the slot 137 of the tether winder member 133 and inserts the tether winder tube 121 back into the internal space 52 of the extender 12E, see FIG. 21. The surgeon rotates the knob 139 of the cable winder one clockwise revolution to ratchet the cable in the cable winder. The cannulated tube 121 may additionally contain a means, such as wheel (see FIG. 22, 178) a bar, a pin, a wheel located at the distal end 125 to limit or prevent unwanted movement of the tether, thereby preventing the tether from ridding up through the tube 121.

Figure 15B:
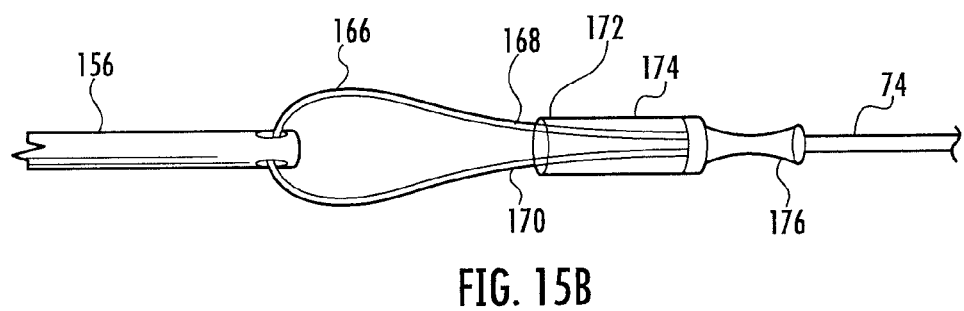
FIG. 15B illustrates the biocompatible device shown in FIG. 15A coupled to the tether member.
Figure 16:
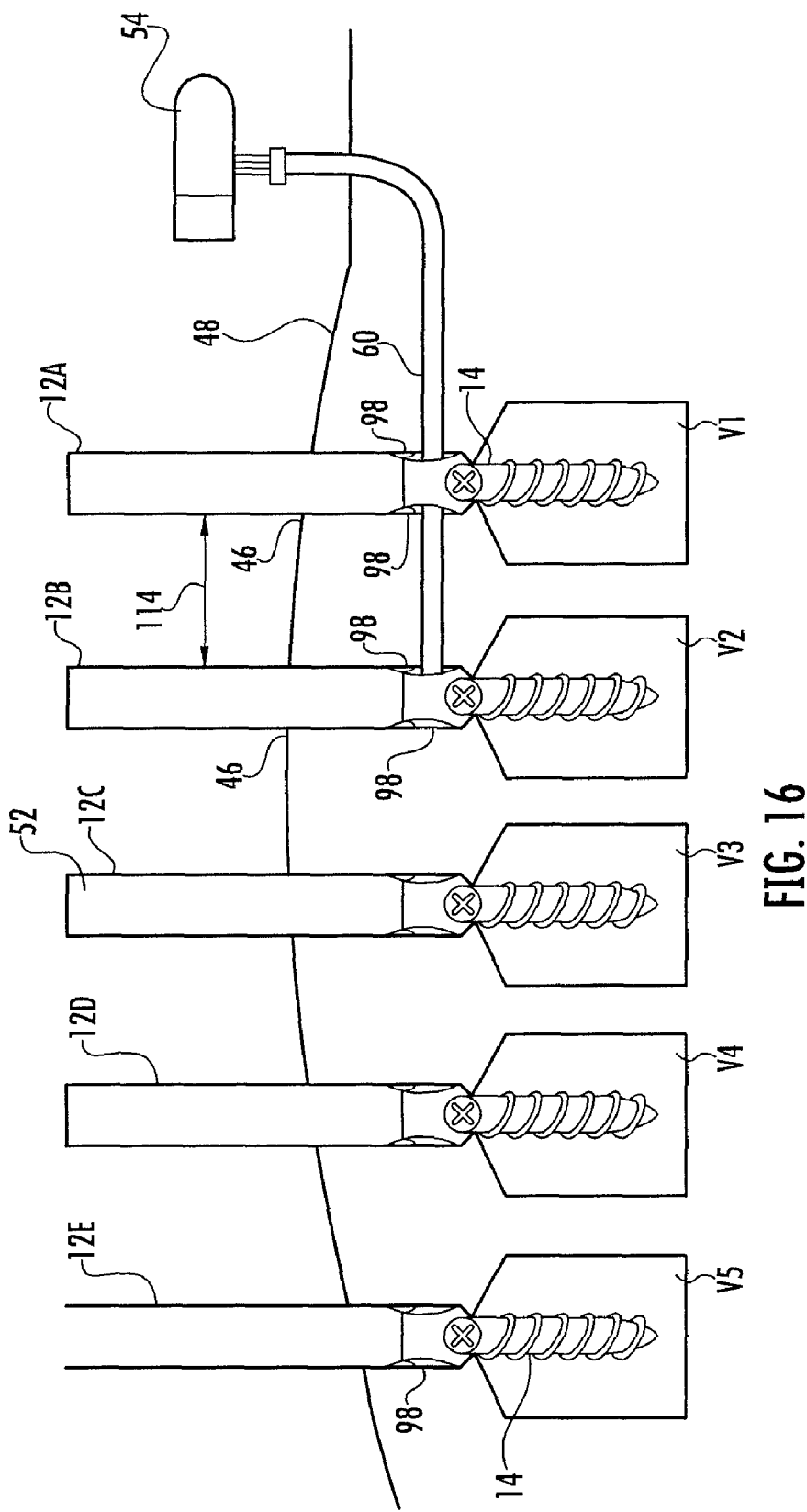
FIG. 16 is a partial side view of a portion of the spine of a patient which includes another embodiment of the system suitable for pulling a biocompatible device to a target area located in vivo in accordance with the instant invention.
Figure 17:
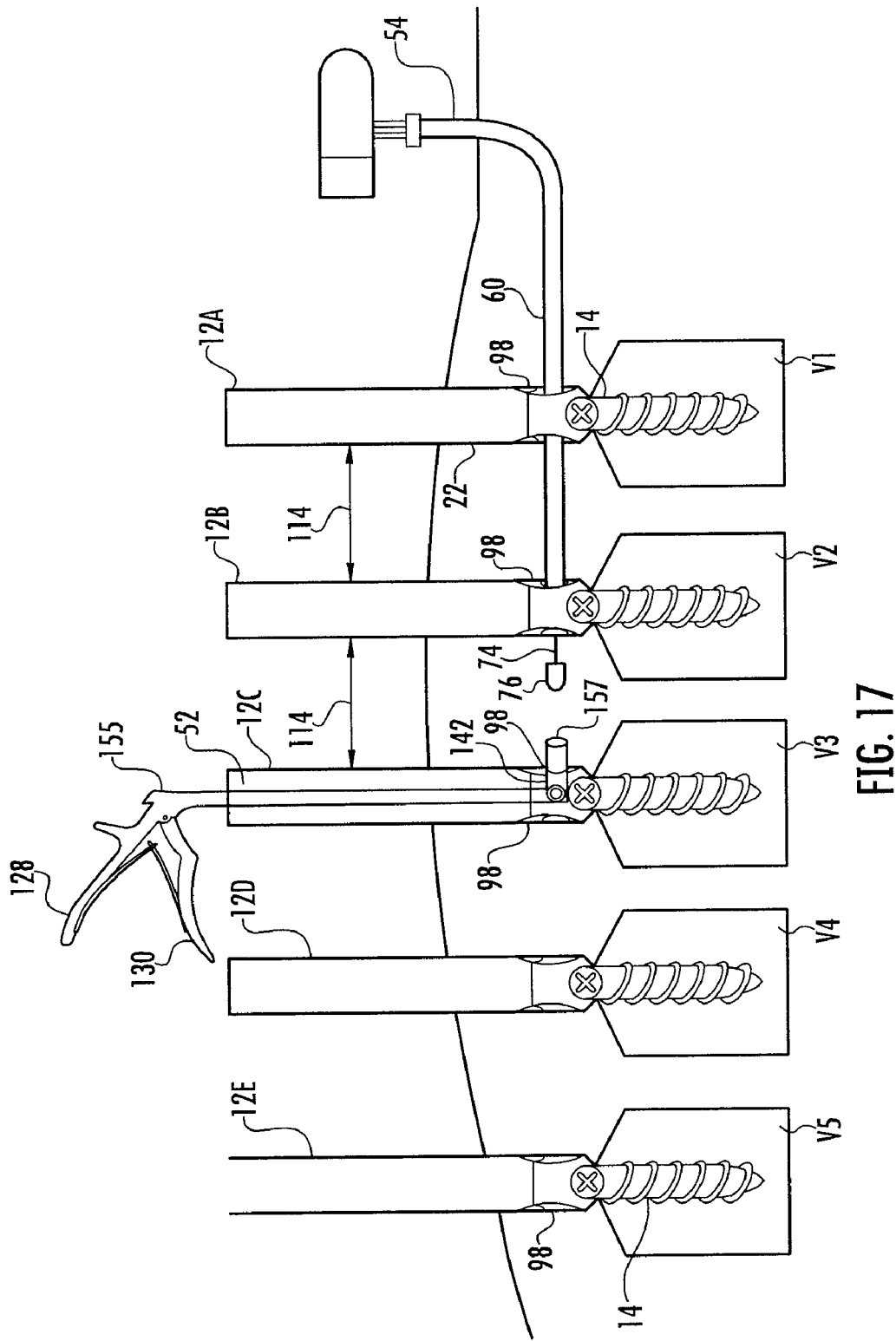
FIG. 17 is the system as shown in FIG. 16, illustrating the insertion of a retrieving device within an extender.

The surgeon then inserts the biocompatible member, illustrated herein as a rod 156, to the end of the tether 74 which was previously coupled to the magnetic introducer 54. After removal of the introducer 54, the tether 74 is inserted into the crimp sleeve 174. Using a device to crimp the sleeve, the surgeon secures the cable end in the sleeve with additional successive adjacent crimps 176 along the sleeve 172 as shown in FIG. 15B. As described previously, the crimped sleeve 174 effectively couples the tether 74 to the rod 156 through cable 166. The surgeon then winds the tether portion coupled to the tether winder which results in the cable moving the rod from the opposite end, thus pulling the rod through the securing anchors 14, see FIGS. 22-23. Once the tether winder has pulled the rod tight, the surgeon releases the tension on the tether and pushes the rod until it is properly positioned for tightening with a screw set. The surgeon then fastens the rod to the anchor members 14 with a screw set that has been lowered into place through the tether winder tube 121. The surgeon then cuts the tether with the tether winder still in place. The cable is then removed from the tube. The surgeon may then fasten the other anchoring members if not already performed.

Any of the aforementioned embodiments of the system and techniques of the present invention can employ any type of known imaging system to determine and locate placement of any of the aforementioned structures in vivo. For example, insertion of the anchor member into the bony structure can be pre-planned by CT scan, x-ray, or the imaging means known in the art.

The present system may also include a feedback system having at least one detection element 180 (two are shown in FIG. 1) disposed outside and proximate the patient to determine the position of the targeting member and/or biocompatible member in real-time. According to one, albeit non-limiting embodiment, the detection element is an audio receiver or pickup capable of audibly detecting when the targeting member and magnetic means connect or "click" together. This way, the surgeon can imagelessly determine that the targeting member has reached the magnetized portion of the anchoring member. This may be used in conjunction with a tactile sensation produced when the targeting member and magnetic means connect. This tactile sensation of the two elements meeting will be felt by the person holding the tethering means.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A system suitable for pulling a biocompatible device to a target area located in vivo comprising: a targeting member, said targeting member having a first end and a second end, said first end being constructed and arranged to penetrate and create a pathway through tissue, said second end constructed and arranged for attachment to a tether; a tether, said tether including a first end, a second end, and an intermediate portion, said first end of said tether secured to said second end of said targeting member, said second end of said tether removably secured to a winding mechanism, said intermediate portion of said tether having a length sufficient to extend through said target area; an extender having a proximal open end, a distal open end, and a cavity there between, said distal open end of said extender being removably attached to a proximal end of an anchoring member, said anchoring member including a passageway, the proximal open end of said extender protruding a distance outside of a percutaneous exposure created on outer skin of a patient; a cannulated introducer constructed and arranged to contain at least a portion of said targeting member or said tether therein, said introducer including a first end, a second open end, and an intermediate section, said targeting member resting at or near said first end, said second open end removably coupled to a handle, said handle having a rotatable knob in operative communication with said winding mechanism, said winding mechanism supporting said tether in a taut position, a loose position, or combinations thereof, said introducer configured to introduce said targeting member and said tether through said passageway of said anchoring member to said target area; one or more retrieving tools, wherein said retrieving tool is a wand, said wand including a magnetic catcher constructed and arranged to cooperate with said targeting member for penetrating and creating said pathway through said tissue, wherein said targeting member includes a magnetically influenced material; a tether winding device tube, said winding device tube having an open distal end, an open proximal end, and a main body there between, said proximal end removably coupled to a rotatable tether winding device, wherein said rotatable tether winding device configured to wind said tether and pull said biocompatible device along said pathway created by said targeting member through said tissue; wherein said biocompatible device including a first end, a second end and an intermediate portion, said first end adapted for connection to said tether after removal of said introducer and said winding mechanism, said intermediate portion being constructed and arranged for attachment to said target area in vivo; a connecting member, said connecting member constructed and arranged for coupling said biocompatible device and said tether; and said anchoring member configured to secure said intermediate portion of said biocompatible device to said target area.

2. The system suitable for pulling a biocompatible device to a target area located in vivo according to claim 1 wherein said tether is a single cable.

3. The system suitable for pulling a biocompatible device to a target area located in vivo according to claim 1 wherein said tether is a multi-strand cable.

4. The system suitable for pulling a biocompatible device to a target area located in vivo according to claim 3 wherein said tether is a cord.

5. The system suitable for pulling a biocompatible device to a target area located in vivo according to claim 1 wherein said biocompatible device is a spinal implant.

6. The system suitable for pulling a biocompatible device to a target area located in vivo according to claim 5 wherein said spinal implant is a rod.

7. The system suitable for pulling a biocompatible device to a target area located in vivo according to claim 5 wherein said spinal implant is a plate.

8. The system suitable for pulling a biocompatible device to a target area located in vivo according to claim 5 wherein said spinal implant is a hook.

9. The system suitable for pulling a biocompatible device to a target area located in vivo according to claim 1 wherein said connecting device for coupling said tether and said biocompatible device is a crimpable sleeve.

10. The system suitable for pulling a biocompatible device to a target area located in vivo according to claim 1 wherein said connecting device for coupling said tether and said biocompatible device is a clamp.

11. The system suitable for pulling a biocompatible device to a target area located in vivo according to claim 1 wherein said connecting device for coupling said tether and said biocompatible device is a hook.

12. The system suitable for pulling a biocompatible device to a target area located in vivo according to claim 1 wherein said retrieving device includes a hand holding grip and a trigger like component pivotally attached thereto, said hand holding grip member including a first elongated rod like member, an additional elongated rod like member is positioned adjacent said first elongated rod member and is pivotally connected to said trigger like component and is also pivotally connected to said magnetic catcher through a pivot at an opposite end, said catcher is also pivotally connected to said additional elongated rod, whereby pivotal motion of trigger like component relative to said hand grip causes relative axial displacement of said first rod like member with respect to said additional rod like member, and said relative displacement will result in pivotal movement of said magnetic catch.

13. The system suitable for pulling a targeting device to a treatment area in vivo according to claim 1 further including a passing device, said passing device constructed and arranged to pass said targeting member within said extender.

14. The system suitable for pulling a targeting device to a treatment area in vivo according to claim 13, wherein said passing device including a hand holding grip and a trigger like component pivotally attached thereto, said hand holding grip member includes an first elongated rod like member, an additional elongated rod like member is positioned adjacent said first elongated rod member and is pivotally connected to said trigger like component and is also pivotally connected to a passing member through a pivot at an opposite end, said passing member constructed and arranged to secure to said targeting member, said passing member is also pivotally connected to said additional elongated rod, whereby pivotal motion of trigger like component relative to said hand grip causes relative axial displacement of said first rod like member with respect to said additional rod like member, and said relative displacement will result in pivotal movement of said passing member.

15. The system suitable for pulling a targeting device to a treatment area in vivo according to claim 1 wherein said extender is sized and shaped to receive said retrieving tool, a passing device, or said winding device tube.

16. The system suitable for pulling a targeting device to a treatment area in vivo according to claim 1 wherein said targeting device is bullet shaped.

17. The system suitable for pulling a targeting device to a treatment area in vivo according to claim 1 wherein said at least one anchoring member for securing said intermediate portion of said biocompatible device to said target area includes a magnetic material effective for attracting said targeting device.

* * * * *